(12) United States Patent
Shibata et al.

(10) Patent No.: US 6,761,698 B2
(45) Date of Patent: Jul. 13, 2004

(54) ULTRASONIC OPERATION SYSTEM

(75) Inventors: Norikiyo Shibata, Yamato (JP);
Mitsumasa Okada, Hachioji (JP);
Manabu Ishikawa, Akiruno (JP);
Tomohisa Sakurai, Sagamihara (JP);
Hitoshi Karasawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 266 days.

(21) Appl. No.: 09/916,622

(22) Filed: Jul. 27, 2001

(65) Prior Publication Data

US 2002/0107538 A1 Aug. 8, 2002

(30) Foreign Application Priority Data

Jul. 28, 2000 (JP) ........................................ 2000-229296
Jun. 12, 2001 (JP) ........................................ 2001-177371
Jun. 18, 2001 (JP) ........................................ 2001-183790

(51) Int. Cl.[7] ............................................. A61B 17/36
(52) U.S. Cl. ........................... 601/2; 600/439; 604/22; 606/1; 606/169
(58) Field of Search ................................. 600/407, 437, 600/439; 601/2, 3, 4; 604/22; 606/169; 433/98, 99, 101, 114, 118, 119

(56) References Cited

U.S. PATENT DOCUMENTS

| 4,552,143 A | 11/1985 | Lottick |
| 5,015,227 A | 5/1991 | Broadwin et al. |
| 5,151,085 A * | 9/1992 | Sakurai et al. ................ 604/22 |
| 5,391,144 A * | 2/1995 | Sakurai et al. ................ 604/22 |
| 5,425,704 A * | 6/1995 | Sakurai et al. ................ 604/22 |
| 5,433,702 A | 7/1995 | Zelman et al. |
| 5,657,761 A * | 8/1997 | Okada et al. ................ 600/437 |
| 5,776,155 A | 7/1998 | Beaupre et al. |
| 2003/0165794 A1 * | 9/2003 | Matoba ...................... 433/114 |

FOREIGN PATENT DOCUMENTS

| JP | H6-42893 | 6/1994 |
| JP | H9-38098 | 2/1997 |
| JP | 2608692 | 2/1997 |
| JP | 2000-271135 | 10/2000 |
| JP | 2001-87276 | 4/2001 |

* cited by examiner

*Primary Examiner*—Eleni Mantis Mercader
(74) *Attorney, Agent, or Firm*—Scully, Scott, Murphy & Presser

(57) ABSTRACT

An ultrasonic operation system includes: a transmission cable that is connected detachably, through a connector, to a connector receptacle in a main apparatus unit; plural types of transducers provided with a connector receptacle each capable of detachably connecting the connector of the transmission cable, an identification element for outputting its own identification signal, and a ultrasonic vibrator, correspondingly; and a main apparatus unit for receiving the identification signals in an identification circuit, automatically controlling drive signals that a control circuit causes a drive signal generator unit to generate, and automatically displaying the identified instrument on a control-display unit.

19 Claims, 23 Drawing Sheets

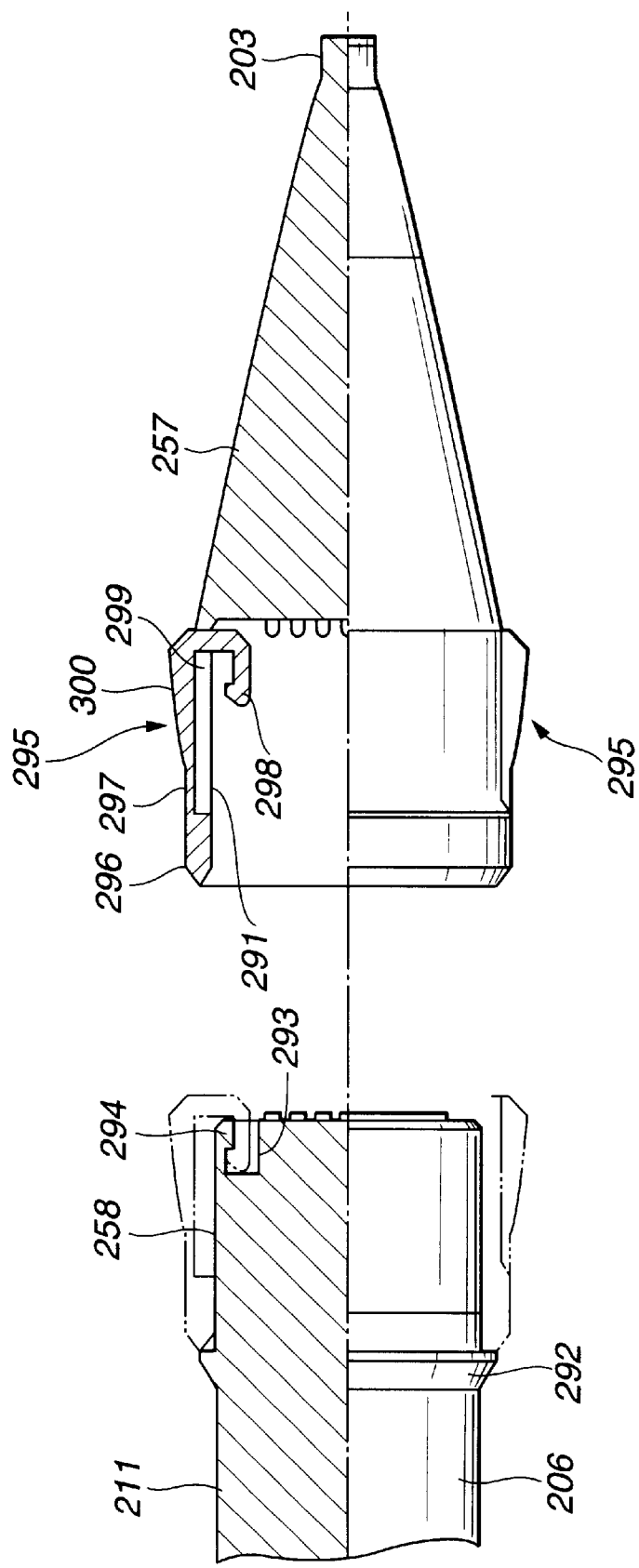

ULTRASONIC OPERATION SYSTEM

This application claims benefit of Japanese Application No. 2000-229296 filed in Japan on Jul. 28, 2000, Japanese Application No. 2001-177371 filed in Japan on Jun. 12, 2001, and Japanese Application No. 2001-183790 filed in Japan on Jun. 18, 2001, the contents of which are incorporated by this reference.

BACKGROUND OF THE INVENTION

1. Field of the Invention

This invention relates to an ultrasonic surgical operation system for generating ultrasonic vibrations and performing treatments on living tissue.

2. Description of the Related Art

Ultrasonic operation systems are being developed, practically implemented, and widely used as surgical operating apparatuses replacing the electric scalpel. These systems can perform such treatments as coagulation, incision, and puncture, using ultrasonic vibrations or other energy.

An example of such a surgical operation apparatus that uses ultrasonic is disclosed in Japanese Patent Application Laid-Open No. H9-38098. This is an operation apparatus wherewith a hand piece having an ultrasonic vibrator incorporated therein is attached to the main apparatus unit, ultrasonic vibrations are generated in the ultrasonic vibrator by driving signals output from that main apparatus unit, those generated ultrasonic vibrations are transmitted to an operating member at the tip end of the hand piece, that operating member is pressed against the treatment object site, and thereby living tissue is subjected to an operating procedure.

With an ultrasonic operation system such as this, as the range of applications has broadened, there are now many types of hand pieces that can be used. Thereupon, in order to meet the demand to be able to use various hand pieces in one surgical operation, configurations are being proposed wherewith multiple hand pieces are connected to the main apparatus unit.

When such multiple types of hand pieces are used, it has been necessary to perform a task to change the way connectors provided at the ends of cords extending from the hand pieces are connected to the main apparatus unit.

An expansion unit has also been proposed, with a view to cases where a plurality of hand pieces is used during one surgical operation, wherewith multiple hand pieces are attached to the main apparatus unit so that use can be made thereof, switching from one hand piece to another.

An example of this kind of thing is disclosed in Japanese Patent Application Laid-Open No. 2000-271135, wherein art is described for providing three connector ports, so that, by manipulating a selector switch provided on a front panel of an expansion unit, the connector port to be used can be selected, that is, a hand piece connected to a given connector port can be selected. In that same publication, a technology is described wherewith provision is made so that a hand switch for turning the output on and off can be attached to a hand piece, so that, when the hand switch is thrown, the hand piece to which that thrown hand switch is attached is selected.

However, when multiple hand pieces are used, there will be multiple cables extending from the hand pieces in the operating room, whereupon the operating room will possibly become congested.

With the technology described in Japanese Patent Application Laid-Open No. 2000-271135 described above, moreover, in order to select a hand piece for use, the switch on the front panel must be manipulated, but that switch is in a non-sterile area, wherefore a surgical operator actually performing the operation cannot manipulate it, but will have to ask a nurse or other assistant to manipulate it, which is confusing.

Furthermore, the surgical operator will then have to confirm the results of the switch made with the expansion unit by looking at the panel display on the main apparatus unit, but there will be cases where the surgical operator will be in a position from which it is difficult to look at that panel display, whereupon that surgical operator will have to change positions or have an assistant make the confirmation as to which port has actually been selected, which is confusing.

There is also a technology, on the other hand, wherewith a freely detachable connector is provided at the hand piece, the cord is left connected at the main apparatus, and the surgical operator is able to use a hand piece that he or she has selected, from among a plurality of types, and connected, in the sterile area where the operation is being performed. With this technology, however, it is confusing for the nurse who is passing out and taking back instruments to confirm which hand piece the surgical operator has selected and connected to the cord.

It should be noted here that, in general, the output of a hand piece such as described in the foregoing is controlled by operating a foot switch. There are cases, however, where, depending on the type of operating instrument used, it is better to use a hand switch than a foot switch.

Various types of such hand switches have been proposed. Known to the technology are, for example, a hand switch that is formed integrally on the hand piece, such as is described in U.S. Pat. No. 5,015,227 and Japanese Patent Publication No. H6-42893, and a hand switch configured so that it can be freely attached to and detached from the hand piece, as described in U.S. Pat. No. 5,433,702, U.S. Pat. No. 4,552,143, and Japanese Patent Application Laid-Open No. 2001-087276, etc.

However, with a configuration wherein the hand piece cable and the hand switch cable are separate, there will be cases where the operation thereof becomes onerous, as noted below.

For example, one end of the hand piece cable is connected to some operating instrument, and the other end is connected to a generator. Also, a hand switch is attached to the operating instrument, and a hand switch generator plug is connected to the generator. The operating instrument is then used in such an arrangement as this.

Subsequently, the operating instrument, with the hand switch still attached thereto, is detached from one end of the hand piece cable, another operating instrument is connected to that one end of that hand piece cable, and that other operating instrument is used by controlling it by a foot switch. If, at this time, the hand switch that is still attached to the original operating instrument is manipulated, there is a possibility that output will be effected from the other operating instrument currently being used, and measures will have to be taken to deal with that possibility, which is troublesome and leads to surgical operating times becoming lengthy.

Furthermore, with a configuration wherein the hand piece cable and the hand switch cable are separate, the number of cables extending from the hand piece will be two, making the operating room more congested.

In Japanese Patent No. 2608692, moreover, the technology is described wherewith one hand switch cable extends from a hand piece socket provided in one end of the hand piece cable, a hand switch is provided integrally at the end of that hand piece cable, and that hand switch can be attached to and detached from the hand piece.

With the technology described in the U.S. Pat. No. 2,608,692, however, the hand switch and the hand switch cable are made integral with the hand piece cable, wherefore it is not possible to select a hand switch of optimal shape according to the operating instrument that is to be attached, the operability of the operating instrument itself may be caused to deteriorate, and there may be cases where that operating instrument cannot be attached. Furthermore, even in the case of an operating instrument that does not require a hand switch, because the hand switch is integrated therewith, it has to be attached to the hand piece, and there is a possibility that it will get in the way.

An ultrasonic operation apparatus in an ultrasonic operation system such as described above will generally comprise a hand piece having an ultrasonic vibrator incorporated therein, and an ultrasonic vibration transmission member for transmitting ultrasonic vibrations to the operating member, which hand piece and ultrasonic vibration transmission member are configured as separate members. Also, provision is made so that, to a horn provided in the hand piece for the purpose of increasing the amplitude of the ultrasonic vibrations, a probe configured of a separate member can be connected, by screwing it in, for example, such that it can be detached.

Cases where a surgical operation is performed using such an ultrasonic operation apparatus as this are not limited to those where a single ultrasonic operation apparatus is used. In surgical operations performed with the use of a laparoscope, for example, multiple ultrasonic trocar outer cannulas are used which may be of different thicknesses. In such cases, an ultrasonic probe (needle) that matches the trocar outer cannula that is to be inserted through the abdominal wall is selected, and the trocar outer cannula is combined together with that ultrasonic probe and used. After it has been passed through the abdominal wall, the trocar outer cannula is left in place and only the ultrasonic probe with the hand piece attached is removed. When it is possible for the ultrasonic probe to be mounted on and used with another trocar outer cannula that is to be inserted next, it can be used as it is, with the hand piece still attached, but when it is to be used with a trocar outer cannula having a different sized diameter, an ultrasonic probe that matches that diameter must be attached to the hand piece for use. This is a troublesome task, and makes it difficult to perform operations quickly.

Other conceivable means include the preparation of multiple sets wherein ultrasonic probes that match a plurality of trocar outer cannulas having different sizes of diameters are respectively combined therewith. In that case, however, the number of output cables connected to the hand pieces becomes plural, and, because there will often be other cables such as high-frequency output cables, water delivery tubes, and air delivery tubes and the like, it becomes a chore to handle all these cables, the different cables will readily become tangled, and the work site will become quite congested.

Furthermore, because there is ordinarily one connector connection port in an ultrasonic oscillating output generator apparatus, a number of tasks must be performed, such as identifying the output cable for the hand piece to be used from a plurality of output cables and connecting the connector thereof to the connector connection port, changing such connections, and verifying the way in which that connection is made, making it quite a chore to find a specific cable among the different tubes that are in the congested state described above. In particular, because the ultrasonic oscillating output generator apparatus will be installed in a position quite removed from the sterilized area where the operation is being performed, those tasks will often have to be delegated to an assistant, and, even when those tasks are delegated to an assistant, liaison therewith is troublesome and inefficient.

Also, ultrasonic probes are usually removed from the hand piece for storage. Thus, every time one is used, a surgical operator or nurse or the like will have to screw a threaded part provided in the base end of the probe into a threaded part in the horn of the hand piece, using a special wrench or other tool, to join the two together.

If the screwing in is not done with the proper force, however, it is possible that the screw connected part will fail during use, due to vibration, just as ultrasonic vibrations are being generated, or that heat will be generated until overheating occurs. For such reasons, there has been an overwhelming tendency to make the screw connection too tight with a wrench. When that screw connection is made too tight, a possibility arises that the screw connection will subsequently fail, or, even if it does not fail, that the ability thereof to transmit vibrations will deteriorate.

Thereupon, special tools have been proposed for maintaining the proper screw tightening force, as described in U.S. Pat. No. 5,776,155, but even when such a tool is used, the problems of the time and trouble required to manage all this remain.

Furthermore, because this is a configuration wherein the ultrasonic probe is attached to the hand piece by a screw-in coupling, there will be cases where, due to the force used when doing the screwing in, the position of the ultrasonic probe about the axis, relative to the hand piece, will become altered. Thus, with a configuration wherein attachment is effected by screwing in, it has been very difficult to always attach the ultrasonic probe to the hand piece such that the two are lined up in a certain way.

When the shape of the operating member of the ultrasonic probe is not equal around the axis, in cases where, as with an ultrasonic trocar, for example, the blade tip is formed so as to be slightly flat in order to make the puncture so as to part the tissue along the grain thereof, it is often necessary to rotate the hand piece being held so as to change the way the operating member of the ultrasonic probe is oriented. For that reason, it is virtually impossible to continually hold the hand piece comfortably in the same position in a similar attitude. In other words, in view of the necessity to change the way the hand piece is held, while verifying the orientation of the operating member of the ultrasonic probe for each instrument, there have been cases where it was very difficult to hold and use the hand piece in a position where it was easy to work.

Meanwhile, in order to detect the utilization limit of an ultrasonic operation apparatus, a technology is being developed wherewith information specific to a hand piece is monitored at the ultrasonic oscillating output generator apparatus that supplies the electric drive power to that hand piece, the number of times the hand piece is used and the condition of such use are recorded, and that record is used to determine when the utilization limit has been reached.

It is very difficult, with such technology for monitoring information specific to a hand piece, to monitor the amount of use and the remaining life and so forth of a probe that is a separate member from that hand piece, but it is a fact that the durability performance of the probe is often lower than the durability performance of the hand piece. That being so, even when an effort is made to replace only the probe, it has not been possible to accurately determine when to make that replacement and thus deal with the problem.

Therefore, with the technology described in the foregoing, it has not been possible to configure an ultrasonic surgical operation system of sufficiently good operability, and it is safe to say that there is room for further improvement.

SUMMARY OF THE INVENTION

An object of the present invention is to provide an ultrasonic surgical operation system exhibiting good operability.

The present invention, simply described, is an ultrasonic operation system comprising: a drive signal generator unit comprising: a drive signal oscillator circuit for generating drive signals for driving an ultrasonic vibrator; and a first connector receptacle for outputting drive signals generated by that drive signal oscillator circuit; a transmission cable comprising: first connector means that are for transmitting the drive signals and that detachably connect to the first connector receptacle; and second connector means for outputting transmitted drive signals; a first hand piece comprising: a second connector receptacle that detachably connects to the second connector means; a first ultrasonic vibrator that vibrates ultrasonically in response to the drive signals input from that second connector receptacle; and a first probe for transmitting the ultrasonic vibrations generated by the first ultrasonic vibrator to the subject body; and a second hand piece comprising: a third connector receptacle that detachably connects to the second connector means; a second ultrasonic vibrator that vibrates ultrasonically in response to the drive signals input from that third connector receptacle; and a second probe, of a shape different from that of the first probe, for transmitting the ultrasonic vibrations generated by the second ultrasonic vibrator to the subject body.

These object(s) and advantages of the present invention will become further apparent from the following detailed explanation.

BRIEF DESCRIPTION OF THE DRAWINGS

FIG. 23 is a side elevation that represents, partially in cross-section, a connection structure for a hand piece and a cable connector in the ultrasonic operation system in the ninth embodiment aspect, in its disassembled condition;

DESCRIPTION OF THE PREFERRED EMBODIMENTS

Embodiment aspects of the present invention are now described with reference to the drawings.

Figure 1:
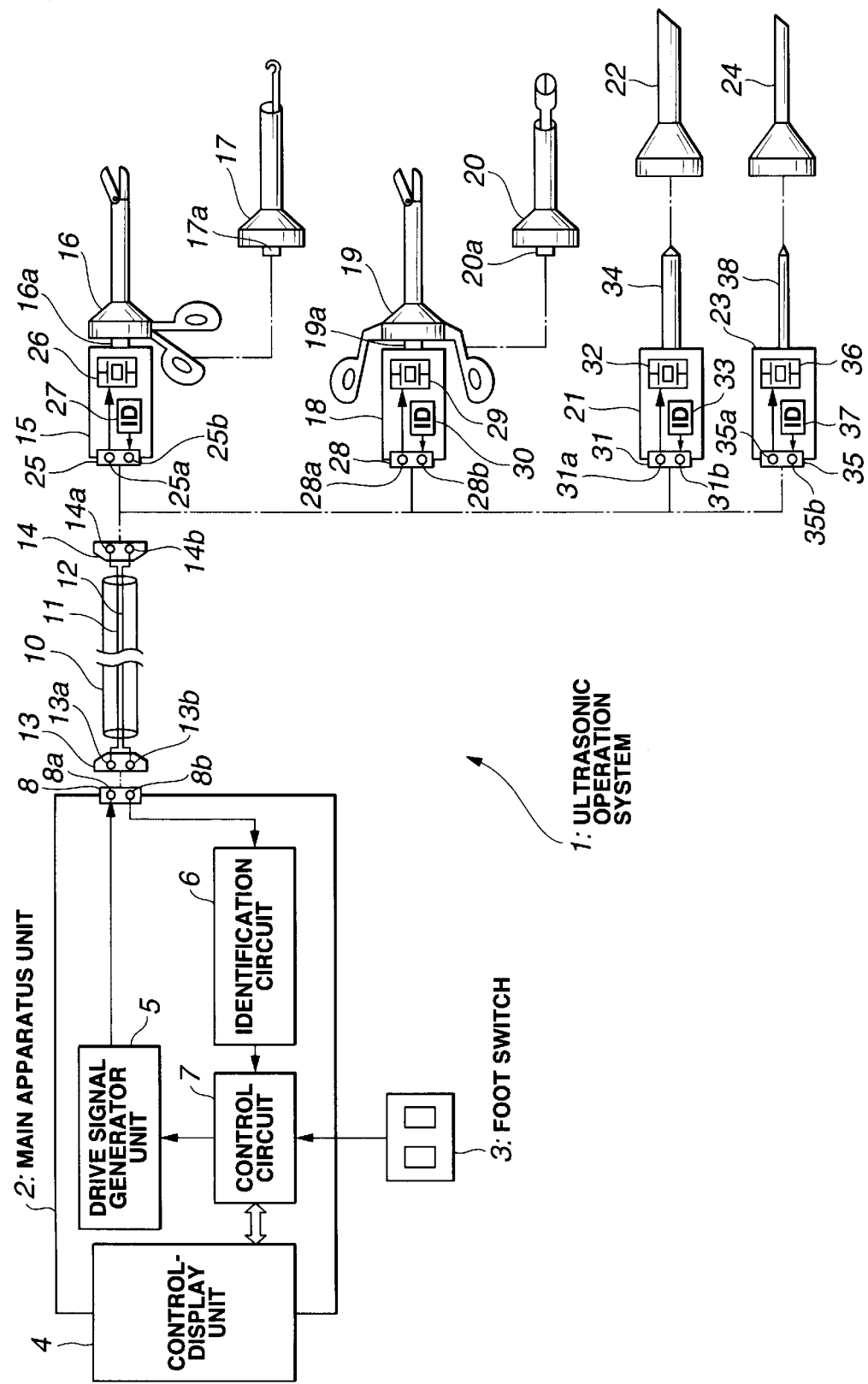
FIG. 1 is a diagram that uses blocks to represent parts of the configuration of an ultrasonic operation system in a first embodiment aspect of the present invention.
Figure 2:
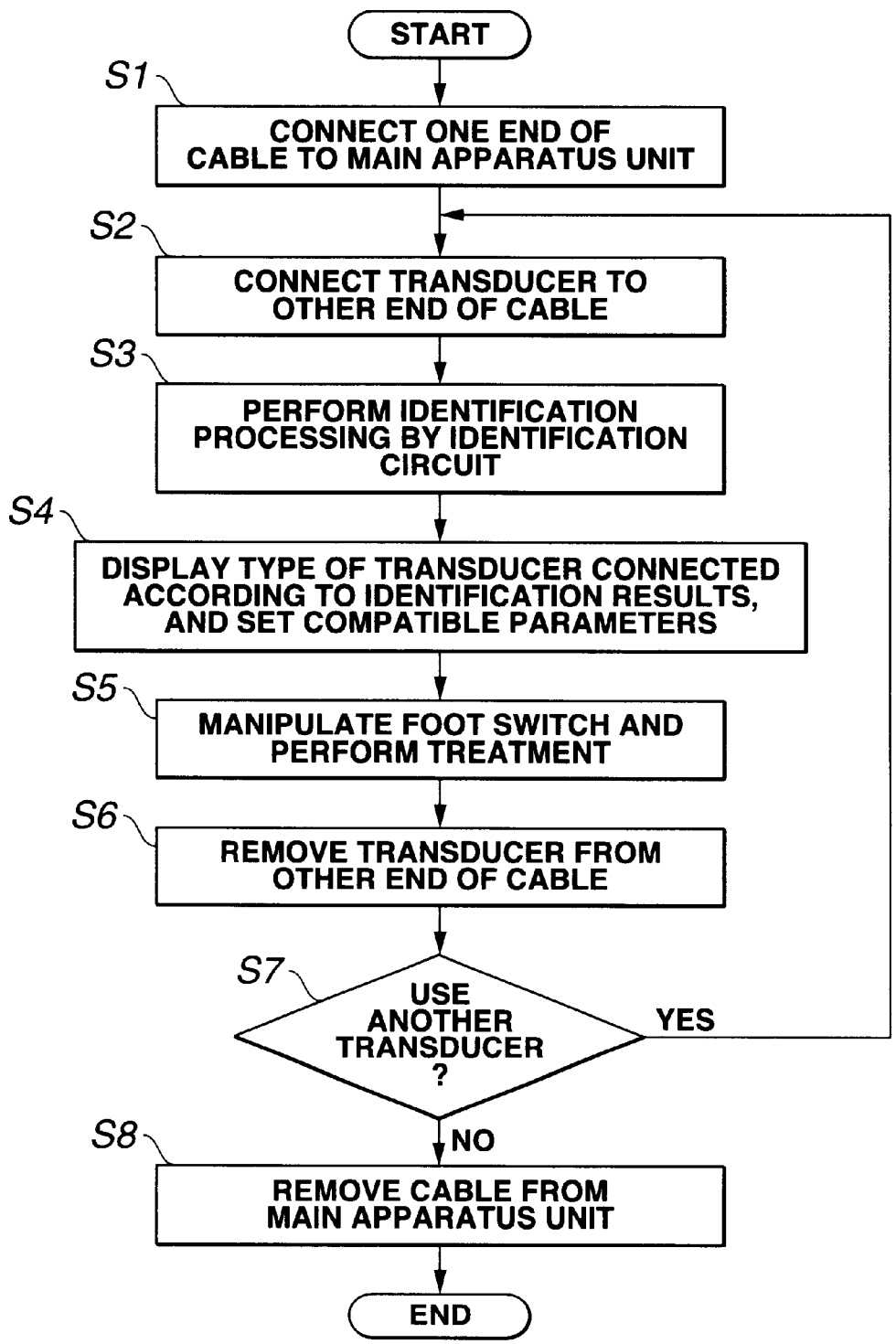
FIG. 2 is a flowchart representing the flow of technology used in the ultrasonic operation system of the first embodiment aspect.
Figure 3:
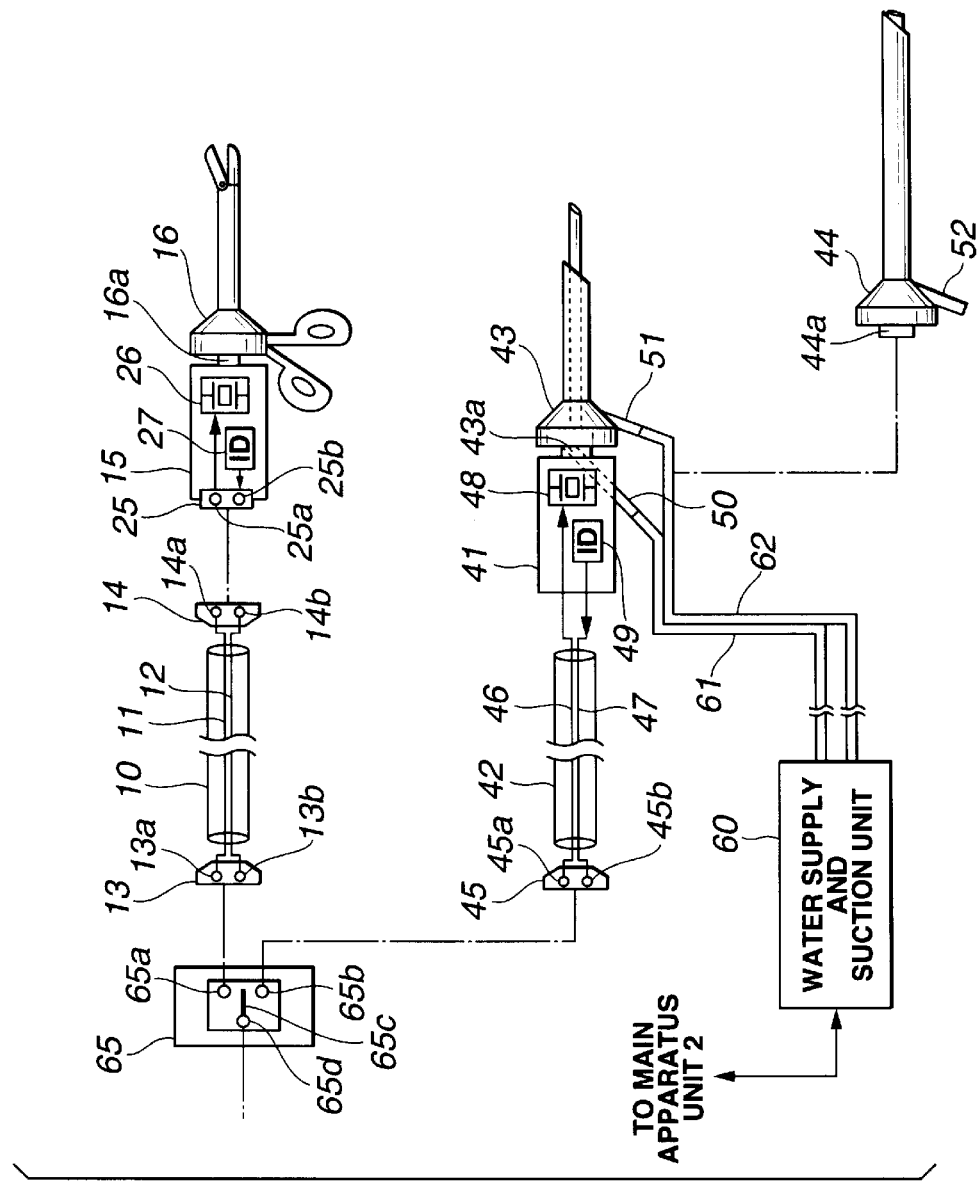
FIG. 3 is a diagram of an example configuration of another hand piece in the ultrasonic operation system of the first embodiment aspect.

FIGS. 1 to 3 represent a first embodiment aspect of the present invention. FIG. 1 is a diagram that uses blocks to represent parts of the configuration of an ultrasonic operation system, FIG. 2 is a flowchart representing the flow of technology used in the ultrasonic operation system shown in FIG. 2, and FIG. 3 is a diagram of an example configuration of another hand piece.

This ultrasonic operation system 1, as shown in FIG. 1, is configured such that a hand piece 9 and a main apparatus unit 2 to which a foot switch 3 is connected are detachably connected through a transmission cable 10.

In this main apparatus unit 2, on the front side thereof, is deployed a control-display unit 4 comprising control switches for making control inputs and a display panel constituting information display means for displaying the operating conditions of this ultrasonic operation system 1. In the outer cover thereof is provided a connector receptacle (first connector receptacle) 8 for connecting the hand piece 9 through the transmission cable 10. Provided internally therein are a drive signal generator unit 5 for generating drive signals for driving an ultrasonic vibrator in the hand piece 9, an identification or identifying circuit 6 that constitutes a part of control means for identifying the type of a connected hand piece 9 by detecting an identification element provided in the hand piece 9, and a control circuit 7 that constitutes a part of control means for receiving inputs from the foot switch 3 and effecting control so that the drive signal generator unit 5 is made to generate drive signals, controlling those drive signals on the basis of the identification results of the identification circuit 6 at that time, and also controlling the other circuits in this main apparatus unit 2.

In the connector receptacle 8 of the main apparatus unit 2 are provided a signal terminal 8a that constitutes the output terminal (first drive signal output terminal) for drive signals generated from the drive signal generator unit 5, and a signal terminal 8b that constitutes the input terminal (second identification signal input terminal) for control signals going to the identification circuit 6.

Provision is made so that, to such a connector receptacle 8, a first connector (first connector means) 13 provided at one end of the transmission cable 10 is detachably connected. In that first connector 13, in turn, are provided a signal terminal 13a that constitutes a first drive signal input terminal connected to the signal terminal 8a, and a signal terminal 13b that constitutes a second identification signal output terminal connected to the signal terminal 8b.

The transmission cable 10 is configured so as to comprise at least a drive signal line 11 that is connected to the signal terminal 13a and constitutes a drive signal transmission cable for transmitting drive signals generated from the drive signal generator unit 5, and an identification signal line 12 that is connected to the signal terminal 13b and constitutes an identification signal transmission cable for transmitting identification signals (identification signals) from the identification element to the identification circuit 6.

At the other end of this transmission cable 10 is provided a second connector (second connector means) 14 for detachably connecting to the transducer (described subsequently) of the hand piece 9. In that second connector 14, in turn, are provided a signal terminal 14a that constitutes a second drive signal output terminal connected to the drive signal line 11, and a signal terminal 14b that constitutes a first identification signal input terminal connected to the identification signal line 12.

The hand piece 9 basically comprises a transducer having an internal ultrasonic vibrator. More precisely, there are two classifications thereof, depending on whether an operating instrument comprising an ultrasonic vibration transmission unit for transmitting ultrasonic vibrations to the transducer is connected separately, or an ultrasonic vibration transmission unit for transmitting ultrasonic vibrations is provided integrally in that transducer.

Firstly, the transducer is basically configured so as to have a connector receptacle comprising multiple signal terminals connected to the signal terminals 14a and 14b, capable of connecting commonly to the second connector 14 irrespective of what type that transducer is, an ultrasonic vibrator for receiving the drive signals and generating ultrasonic vibrations, and an identification element for generating identification information (ID information) indicating which type that transducer is.

More specifically, a first transducer 15 that constitutes transducer means is configured so as to comprise a signal terminal 25a that constitutes a second drive signal input terminal connected to the signal terminal 14a, and a signal terminal 25b that constitutes a first identification signal output terminal connected to the signal terminal 14b, and so as to have a connector receptacle (second connector receptacle) 25 capable of being detachably connected to the second connector 14, an ultrasonic vibrator 26 for receiving the drive signals and generating ultrasonic vibrations, and an identification element 27 that constitutes identification signal generator means for generating identification information indicating the type of the first transducer 15.

To the first transducer 15, as diagrammed, it is possible to detachably and selectively connect a scissors type operating instrument 16 comprising an ultrasonic vibration transmission unit 16a (probe), and a hook type operating instrument 17 comprising an ultrasonic vibration transmission unit 17a (probe). By combining the first transducer 15 and the scissors type operating instrument 16, a scissors type hand piece is configured. And by combining the first transducer 15 and the hook type operating instrument 17, a hook type hand piece is configured.

A second transducer 18 that comprises transducer means is configured similarly so as to have a connector receptacle (second connector receptacle) 28 capable of being detachably connected to the second connector 14, comprising a signal terminal 28a that constitutes a second drive signal input terminal connected to the signal terminal 14a and a signal terminal 28b that constitutes a first identification signal output terminal connected to the signal terminal 14b, an ultrasonic vibrator 29 for receiving the drive signals and generating ultrasonic vibration, and an identification element 30 that constitutes identification signal generator means for generating identification information indicating the type of the second transducer 18.

To that second transducer 18 it is possible to detachably and selectively connect an inline scissors type operating instrument 19 comprising an ultrasonic vibration transmission unit 19*a* (probe), and a spatula type operating instrument 20 comprising an ultrasonic vibration transmission unit 20*a* (probe). By combining the second transducer 18 and the inline scissors type operating instrument 19, an inline scissors type hand piece is configured. By combining the second transducer 18 and the spatula type operating instrument 20, a spatula type hand piece is configured.

Moreover, a third transducer 21 is configured so as to comprise a signal terminal 31*a* that constitutes a third drive signal input terminal connected to the signal terminal 14*a* and a signal terminal 31*b* that comprises a second identification signal output terminal connected to the signal terminal 14*b*, and so as to integrally have a connector receptacle (third connector receptacle) 31 capable of being detachably connected to the second connector 14, an ultrasonic vibrator 32 for receiving the drive signals and generating ultrasonic vibrations, an identification element 33 that constitutes identification signal generator means for generating identification information indicating the type of the third transducer 21, and a large-diameter probe 34 that is an ultrasonic vibration transmission unit for transmitting ultrasonic vibrations generated by the ultrasonic vibrator 32.

This third transducer 21 is such that, by passing the large-diameter probe 34 as an inner needle in the trocar 22 that is a large-diameter outer cannula, a large-diameter trocar-type hand piece is configured.

Also, a fourth transducer 23 is configured so as to comprise a signal terminal 35*a* that constitutes a third drive signal input terminal connected to the signal terminal 14*a* and a signal terminal 35*b* that comprises a second identification signal output terminal connected to the signal terminal 14*b*, and so as to integrally have a connector receptacle (third connector receptacle) 35 capable of being detachably connected to the second connector 14, an ultrasonic vibrator 36 for receiving the drive signals and generating ultrasonic vibrations, an identification element 37 that constitutes identification signal generator means for generating identification information indicating the type of the fourth transducer 23, and a narrow-diameter probe 38 that is an ultrasonic vibration transmission unit for transmitting ultrasonic vibrations generated by the ultrasonic vibrator 36.

This fourth transducer 23 is such that, by passing the narrow-diameter probe 38 as an inner needle in the trocar 24 that is a narrow-diameter outer cannula, a narrow-diameter trocar-type hand piece is configured.

Next, the flow of a surgical operation wherein an ultrasonic operation system such as described in the forgoing is used is described with reference to FIG. 2.

When an operation wherein this ultrasonic operation system is to be used is started, first, the connector 13 of the transmission cable 10 is connected to the connector receptacle 8 of the main apparatus unit 2 (step S1). This connecting task, because it is performed in a non-sterile area, will be performed by a nurse or the like assisting the surgical operator.

Next, in an endoscopic operation, because it is necessary to insert the trocar and secure a port through which to introduce operating instruments inside the body, first, the transducer 23 used in combination with the narrow-diameter trocar 24, for example, is connected to the connector 14 of the transmission cable 10 (step S2). This connecting task, because it is performed in the sterile area, can be performed by the surgical operator himself or herself.

By this connection, identification information will be output from the identification element 37 inside that transducer 23, and input via the identification signal line 12 of the transmission cable 10 to the identification circuit 6. Thus the identification circuit 6 will determine which piece of equipment is connected and output the results of that identification to the control circuit 7 (step S3).

The control circuit 7, receiving those identification results, sets various parameters so that the drive signal generated from the drive signal generator unit 5 will be matched to the determined equipment. At that time, the control circuit 7 will also cause the fact that the transducer 23 is being used in a narrow-diameter trocar type hand piece to be displayed on the control-display unit 4 (step S4).

Thereafter, when the surgical operator manipulates the foot switch 3, a drive signal will be generated from the drive signal generator unit 5, the ultrasonic vibrator 36 will be driven, and the ultrasonic trocar operation will be started (step S5).

Once the insertion of the trocar 24 is finished, the transducer 23 is removed from the connector 14 of the transmission cable 10 (step S6).

Thereafter, according to whether or not another transducer is to be used, the processing will branch (step S7).

That is, when another transducer is to be used, as, for example, when the scissors type hand piece formed by combining the first transducer 15 and the scissors type operating instrument 16 is to be used, processes like those described above in steps S2 to S5 are performed for that first transducer 15.

At that time, due to the process of step S3, it will be determined that the connected instrument is the first transducer 15, and parameters suitable to that first transducer 15 will be automatically set, wherefore there is no need to require the nurse or the like assisting the surgical operator to perform any separate manipulation of the main apparatus unit 2, and it will be possible with great simplicity to change to and use another transducer. Meanwhile, because the type of transducer changed to and the like will be displayed on the control-display unit 4, the nurse or other assistant will be able to readily ascertain that information.

Thus, when the ultrasonic scissors operation by that scissors type hand piece is finished, that first transducer 15 will be removed from the connector 14 of the transmission cable 10 in step S6.

Thereafter, when other transducers are to be used, in like fashion, the processes in steps S2 to S6 will be performed.

Then, in step S7, when a decision is made not to use any more transducers, the transmission cable 10 is removed from the main apparatus unit 2 (step S8).

Next, another hand piece configuration example is described, with reference to FIG. 3. In FIG. 3, those portions that are like those in FIG. 1 are indicated by the same symbols and not further described.

In the configuration shown in FIG. 3, a connector switching device 65 is attached to the connector receptacle 8 of the main apparatus unit 2. Thus provision is made so that switching can be done to handle cases where the scissors type operating instrument 16 and the first transducer 15 are to be used with the transmission cable 10, on the one hand, and cases where a hand piece having another configuration, as described below, is to be used, on the other.

The connector switching device 65 is configured so as to have an input/output point 65a and an input/output point 65b that can be switched between, a switch 65c for switching between those input/output points 65a and 65b, and an input/output point 65d for connecting one or other of the input/output points 65a and 65b selected by the switch 65c to the connector receptacle 8 of the main apparatus unit.

In the example shown here in FIG. 3, the first transducer 15 and the scissors type operating instrument 16 are connected via the transmission cable 10 to the input/output point 65a in the connector switching device 65. This is simply one example, moreover, and there is no problem with connecting another hand piece as shown in FIG. 1.

To the other input/output point, namely 65b, in the connector switching device 65, a hand piece is connected which, comprising a hollow pipe-shaped probe, is designed to emulsify tissue by ultrasonic vibration and remove it by suction.

This hand piece, more particularly, is configured so as to have a transducer 41 that constitutes transducer means, a transmission cable 42 integrated with the transducer 41, and an ultrasonic emulsifying suction operating instrument 43 that constitutes ultrasonic operating means provided for the transducer 41 such that it can be attached and detached freely.

The transmission cable 42 is configured, roughly in the same way as the transmission cable 10, so as to have a connector 45 constituting connector means provided with a signal terminal 45a that constitutes a drive signal input terminal and a signal terminal 45b that constitutes an identification signal output terminal, a drive signal line 46, connected to the signal terminal 45a, that constitutes a drive signal transmission cable for transmitting drive signals generated from the drive signal generator unit 5, and an identification signal line 47, connected to the signal terminal 45b, that constitutes an identification signal transmission cable for transmitting identification signals from the identification element 49 (described below) to the identification circuit 6. Because this transmission cable 42 is provided integrally with the transducer 41, however, no connector is provided at the other end.

The transducer 41, moreover, is configured so as to have an ultrasonic vibrator 48 for receiving drive signals from the drive signal line 46 and causing ultrasonic vibrations to be generated, an identification element 49 that constitutes identification signal generator means for generating identification information indicating the type of the transducer 41 and transmitting that information via the identification signal line 47, and a suction port fitting 50.

The ultrasonic emulsifying suction operating instrument 43, on the other hand, as described already, is provided with a hollow pipe-shaped probe 43a, is configured as a short type of instrument used in open surgical operations for emulsifying tissue by ultrasonic vibration and removing it by suction, and has a water delivery port fitting 51, which is for supplying physiological saline solution for cooling or cleaning, extending from a side surface that forms a tapered shape at the base end.

A suction tube 61 is connected to the suction port fitting 50 and a water delivery tube 62 is connected to the water delivery port fitting 51. These tubes, namely the suction tube 61 and the water delivery tube 62, are connected to a water delivery and suction unit 60 that is necessary when performing ultrasonic emulsification and suction. Thus provision is made so that suction and water delivery can be performed. This water delivery and suction unit 60 is also made so that the operation thereof is controlled by the main apparatus unit 2.

The transducer 41 is also made so that, instead of the ultrasonic emulsifying suction operating instrument 43, an endoscopic operating instrument 44 that constitutes ultrasonic operating means having a length of approximately 20 to 30 cm used in endoscopic surgical operations can be connected thereto. This endoscopic operating instrument 44 is also provided with a hollow pipe-shaped probe 44a, and has a water delivery port fitting 52, which is for supplying physiological saline solution for cooling or cleaning, extending from a side surface that forms a tapered shape at the base end. When the endoscopic operating instrument 44 is to be used, the water delivery tube 62 is connected to that water delivery port fitting 52.

Thus, by adding the water delivery and suction unit 60 while using the main apparatus unit 2 in common, it is possible to configure an ultrasonic suction system.

When an operation is being performed using an ultrasonic operation system like that shown in FIG. 3, a flow like that shown in FIG. 2 will be basically followed, but with the exceptions noted below.

First, that which is connected to the connector receptacle 8 of the main apparatus unit 2 is the connector switching device 65, the connector 13 of the transmission cable 10 is connected to the input/output point 65a of the connector switching device 65, and the connector 45 of the transmission cable 42 is connected to the input/output point 65b.

The connector receptacle 25 of the transducer 15 is connected to the connector 14 of the transmission cable 10, and the scissors type operating instrument 16, for example, is attached to that transducer 15, in the same manner as described earlier.

To the transducer 41, on the other hand, the ultrasonic emulsifying suction operating instrument 43, for example, is connected, whereupon the suction tube 61 will be attached to the suction port fitting 50 and the water delivery tube 62 will be attached to the water delivery port fitting 51.

At this time, furthermore, by connecting that water delivery and suction unit 60 to the main apparatus unit 2, it becomes possible to control the suction or water delivery by the control circuit 7 of the main apparatus unit 2.

After the connections described above have been made, by switching the switch 65c of the connector switching device 65 either to the input/output point 65a or to the input/output point 65b (switched here, for example, to the input/output point 65b side), identification information is output from the identification element 49 in the transducer 41 and input to the identification circuit 6 via the identification signal line 47 of the transmission cable 42.

In this manner, the identification circuit 6 determines which instrument has been connected, and outputs the results of that identification action to the control circuit 7. The control circuit 7, upon receiving those identification results, sets various parameters and the like so that the drive signal generated from the drive signal generator unit 5 is made a drive signal that is compatible with the identified instrument, that being, in this case, the transducer 41 which has the ultrasonic vibrator 48. The control circuit 7 also causes information on the connected instrument to be displayed on the control-display unit 4.

The control circuit 7, furthermore, in response to the identification results, communicates with the water delivery and suction unit 60, sets optimal parameters, and exercises control so that the water delivery and suction actions of the water delivery and suction unit 60 are synchronized with the sending out of the drive signal for the ultrasonic vibrations by the drive signal generator unit 5.

When the switch 65c of the connector switching device 65 is switched to the input/output point 65a side, the identification information output from the identification element 27 is subjected to judgment by the identification circuit 6, and the control circuit 7 that receives those identification results sets parameters that are optimal for the transducer 15 comprising the ultrasonic vibrator 26, and causes information on the connected instrument to be displayed on the control-display unit 4, in the same manner as described earlier.

The transducer 41 and the transmission cable 42 were integrated in order to make the hand piece compact and improve its handling characteristics and other operability factors. More specifically, because it is necessary to attach the suction tube 61 and water delivery tube 62 to the hand piece shown in FIG. 3, providing a connector or connector receptacle will inevitably lead to making the hand piece larger. There is also the consideration that ultrasonic suction treatments, in brain surgery in particular, are often conducted by themselves. Thereupon, taking those circumstances into consideration, the configuration is made one in which the transducer 41 and the transmission cable 42 are integrated and any connectors or connector receptacles are omitted.

Nevertheless, it is also possible to implement such a transducer 41 as this in a connector attaching scheme in the same manner as with the other transducers described earlier.

Conversely, it is also possible to provide the transmission cable 10 integrally in such transducers as the transducers 15, 18, 21, and 23 shown in FIG. 1 and omit therefrom the connectors and connector receptacles.

In the example shown in FIG. 3, furthermore, provision is made so that the scissors type hand piece and the ultrasonic suction hand piece can be used separately during one operation by means of the connector switching device 65. Needless to say, there is no problem at all with using those such that they are directly connected to the connector receptacle 8 of the main apparatus unit 2 as shown in FIG. 1.

It is also possible to configure the connector switching device 65 so that it is incorporated integrally into the water delivery and suction unit 60.

Based on such a first embodiment aspect as this, it becomes possible for a surgical operator to easily and distinguishably use multiple types of hand pieces during one operation, at his or her discretion, whether the transducer is of the type wherewith an operating instrument having an ultrasonic vibration transmission unit is attached and detached or is a transducer wherein the ultrasonic vibration transmission unit is provided integrally therewith. At such time, moreover, as soon as the surgical operator himself or herself has simply connected the hand piece to the transmission cable in the operating theater, parameters for a drive that is optimal to that hand piece are set, wherefore there is no need for any troublesome manipulation to be made, and operability is improved. Also, because the type of the connected hand piece is displayed on the control-display unit, that can be readily verified.

Furthermore, an ultrasonic suction apparatus that conventionally required a large and expensive system can be easily realized by adding a dedicated hand piece and water delivery and suction unit to an existing ultrasonic operation system. When that is done, moreover, by employing a connector switching device, it is also possible to distinguishably use the ultrasonic suction unit and a scissors type hand piece, for example, made for an existing ultrasonic operation system, during the same operation.

Figure 4:
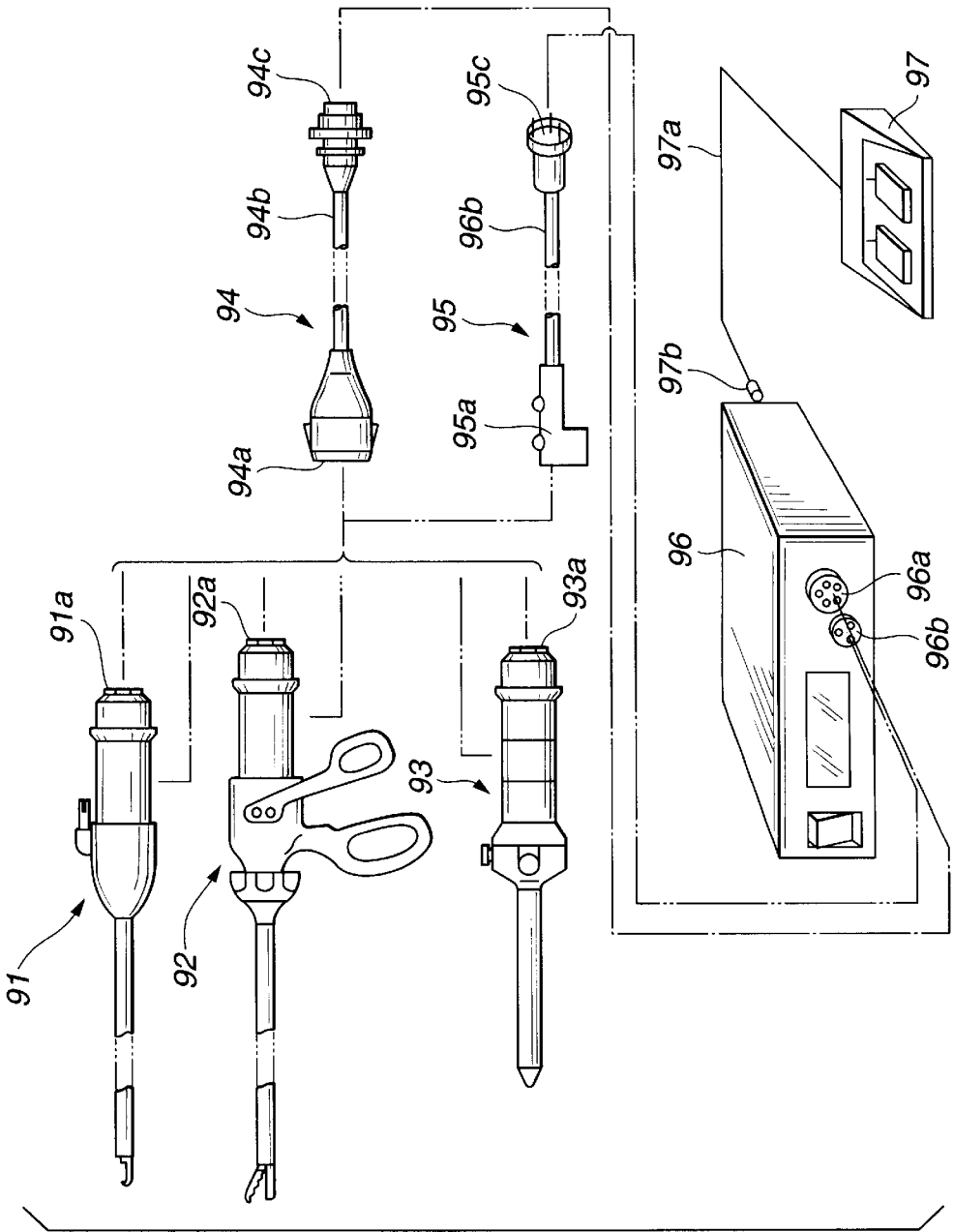
FIG. 4 is a diagram of combination examples in an ultrasonic operation system in a second embodiment aspect of the present invention.

FIG. 4 shows a second embodiment aspect of the present invention. FIG. 4 represents ultrasonic operation system combination examples. In this second embodiment aspect, portions that are the same as in the first embodiment aspect are indicated by the same symbols and not further described here. Mainly the points of difference only are described.

A hand switch that is configured so that it can be freely attached to and detached from a hand piece is described, with reference to FIG. 4.

This ultrasonic operation system is a system, wherein any one of a plurality of types of hand pieces, such as a hook probe type hand piece 91, scissors probe type hand piece 92, or trocar probe type hand piece 93, can be selectively connected to generator 96 through drive energy supply cord 94, and is configured so that a hand switch unit 95 can be detachably connected to the selected hand piece.

More specifically, a common plug shape is implemented in hand piece plugs 91a, 92a, and 93a provided respectively in the hand pieces 91, 92, and 93, so that those hand piece plugs 91a, 92a, and 93a can be connected to a hand piece socket 94a provided in one end of a drive energy supply cord 94.

The drive energy supply cord 94 has the hand piece socket 94a provided at one end of the cable 94b thereof, and a generator plug 94c provided at the other end.

The generator plug 94c is made so that it connects to the hand piece connector 96a provided in a generator 96.

The hand switch unit 95 is configured so that it has a hand switch unit 95a provided with control switches and capable of being attached to the grip portion or the like of the hand pieces 91, 92, and 93, a cable 95b that extends from the hand switch unit 95a, and a hand switch generator plug 95c provided at the other end of that cable 95b.

The hand switch generator plug 95c is made so that it connects to a hand switch connector 96b provided in the generator 96.

This generator 96 is also made so that a foot switch 97 can be detachably connected thereto, and so that settings can be made by connecting a foot switch plug 97b provided in the leading end of a cable 97a that extends from that foot switch 97.

Based on such a second embodiment aspect as this, as with the first embodiment aspect described earlier, it is possible for a surgical operator easily to distinguishably use a plurality of types of hand piece during one operation, at his or her own discretion, but it is further possible to attach a switch unit if required.

In the case of such a second embodiment aspect as described in the foregoing, it should be noted, there will be two cables extending from the hand piece, namely the drive energy cable and the switching cable, whereupon there is a possibility of the operating room becoming congested. That being so, an embodiment aspect is described below that is designed to improve that aspect.

Figure 5:
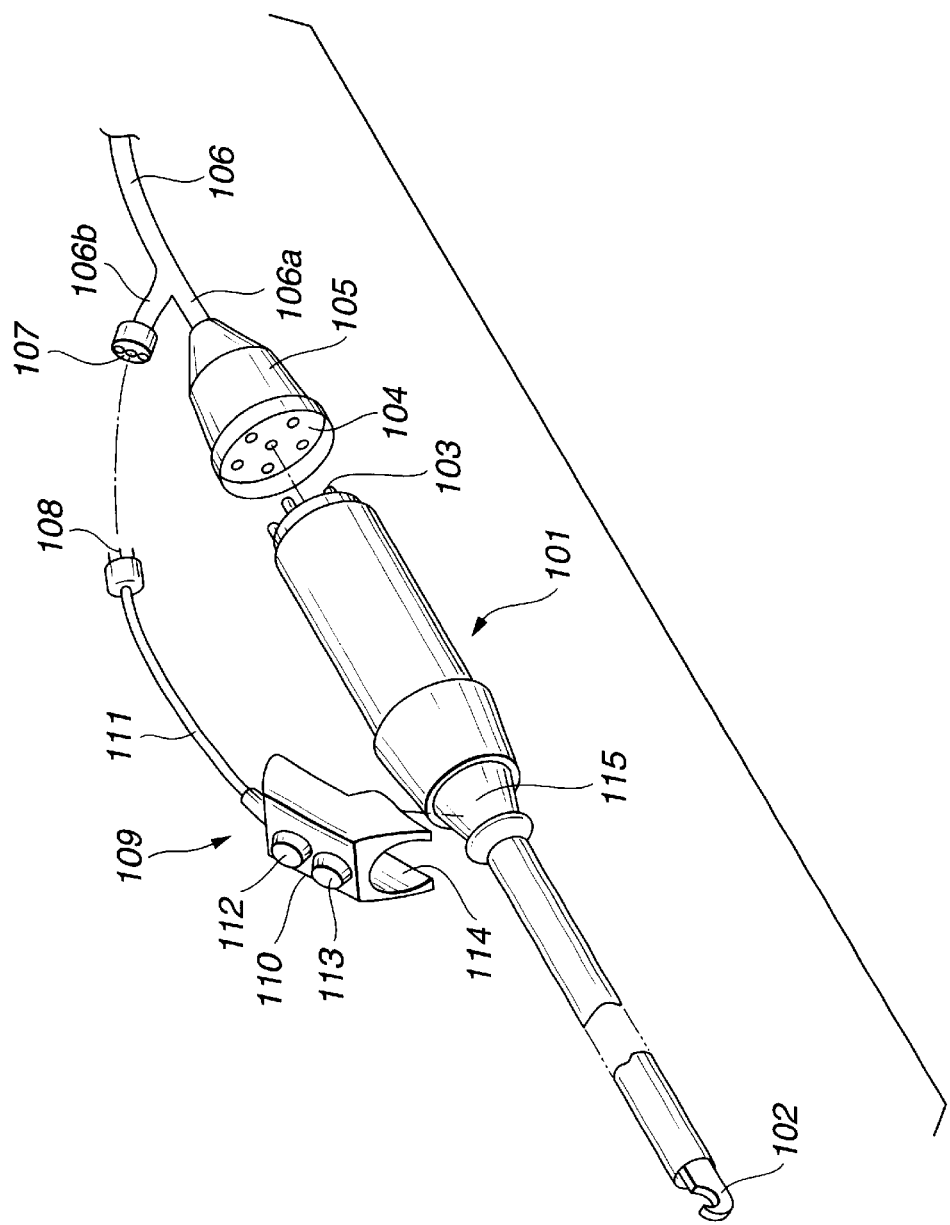
FIG. 5 is a diagonal view of the configuration of a hand piece and hand switch unit in an ultrasonic operation system in a third embodiment aspect of the present invention.
Figure 6:
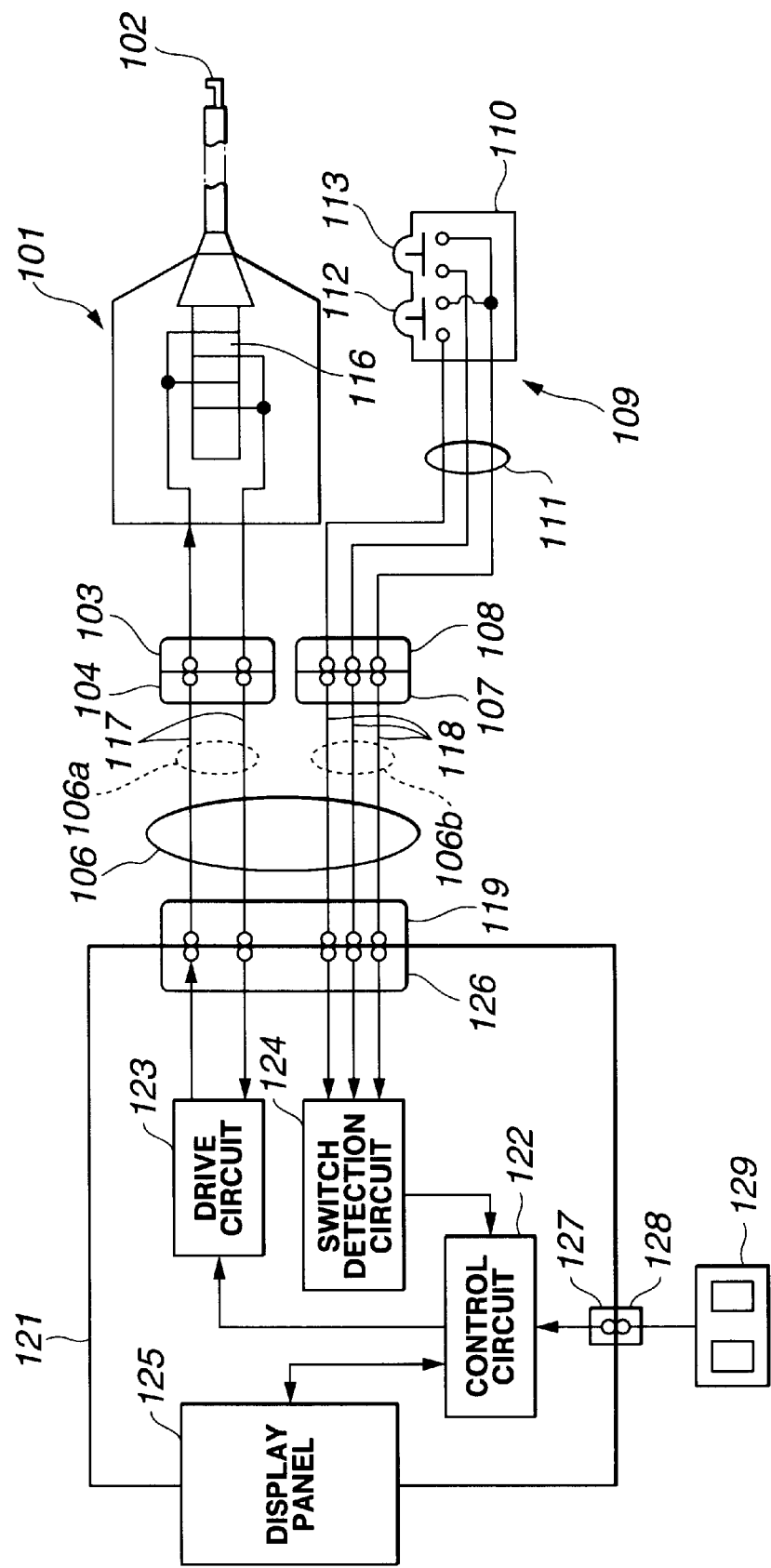
FIG. 6 is a diagram that uses blocks to mainly represent parts of the electrical configuration of an ultrasonic operation system in the third embodiment aspect of the present invention.

FIG. 5 and FIG. 6 show a third embodiment aspect of the present invention. FIG. 5 is a diagonal view of the configuration of a hand piece and a hand switch unit in an ultrasonic operation system, while FIG. 6 is a diagram that uses blocks to mainly represent parts of the electrical configuration of the ultrasonic operation system.

A hand piece 101 that constitutes hand piece means has a long and slender insertion unit extending from the grip part toward the leading end, with a hook-shaped operating member 102 provided in the leading end of that insertion unit. Also, a tapered connecting part 115 is provided at the leading end of the grip part of the hand piece 101, and a hand piece plug 103 constituting a second connector receptacle having a second energy signal input terminal for inputting drive signals that are operating energy signals is provided at the back end thereof.

This hand piece 101 also has incorporated into it an ultrasonic vibrator 116 for generating ultrasonic vibrations (see FIG. 6), and an ultrasonic vibration transmission unit for transmitting the ultrasonic vibrations generated by that ultrasonic vibrator 116 to the operating member 102.

The hand piece plug 103 is for inputting drive signals for driving the ultrasonic vibrator 116, and is made so that it can be detachably connected to a drive signal plug 104 of a hand piece socket 105, that drive signal plug 104 constituting second connector means having a second energy signal output terminal.

The hand piece socket 105 is provided in one branching end 106a of a transmission cable 106 that is a drive energy supply cord for transmitting drive signals output from a generator 121 (see FIG. 6) described subsequently, and a hand switch input plug 107 constituting third connector means having a first switching signal input terminal is provided in the other branching end 106b of that transmission cable 106.

The hand switch input plug 107 is made so that an output plug 108 constituting a third connector receptacle having a first switching signal output terminal in a hand switch unit 109 constituting a switching switch unit can be detachably connected thereto, and it is possible to transmit signals from that hand switch unit 109 to the generator 121.

The hand switch unit 109, which is a main switch unit for making control inputs to control the output of ultrasonic vibrations, is configured so as to comprise a hand switch unit 110 that constitutes a hand switch relay, a hand switch cable 111 that extends from the hand switch unit 110, and the output plug 108 provided in the end of this hand switch cable 111.

The hand switch unit 110 comprises a setting value output button 112 for making control inputs so that outputs determined by predetermined setting values are effected, a 100% output button 113 for making a control input so that the maximum output is continually effected, and a mounting piece 114 that constitutes connecting means of a snap fitting form for joining the hand switch unit 110 to the connecting part 115.

Next, the circuit configuration of an ultrasonic operation system comprising a hand piece 101 and generator 121 such as described above is described with reference to FIG. 6.

At the other end of the transmission cable 106 is provided a generator plug 119 constituting first connector means having a first energy signal input terminal and a second switching signal output terminal, with provision made so that it can be detachably connected to a hand piece connector 126 in the generator 121. Inside the transmission cable 106 are provided a drive signal line 117 that constitutes a drive signal transmission line for transmitting drive signals that are operating energy signals, and a hand switch signal line 118 that constitutes a control signal transmission line for transmitting hand switch signals (control signals or switching signals). Provision is made, furthermore, so that, after this transmission cable 106 branches at the leading end thereof, the drive signal line 117 is provided at the branching end 106a, and the hand switch signal line 118 is provided at the branching end 106b.

The generator 121 is made so that a foot switch 129 is connected by connecting a foot switch plug 128.

The generator 121 is configured so as to comprise the hand piece connector 126 that constitutes a first connector receptacle having a first energy signal output terminal and a second switching signal input terminal and is for connecting the generator plug 119, a foot switch connector 127 for connecting the foot switch plug 128, a drive circuit 123 that comprises operating energy signal generator means for generating and outputting drive signals for driving the ultrasonic vibrator 116, a switch detection circuit 124 for detecting that either the setting value output button 112 or the 100% output button 113 of the hand switch unit 109 has been depressed, a display panel 125, provided so as to be exposed on the outer cover of the generator 121, for effecting displays relating to this ultrasonic operation system, and a control circuit 122 that constitutes control means for controlling the drive circuit 123 and the display panel 125 on the basis of signals output from the switch detection circuit 124, control signals input from the foot switch 129 (described subsequently), or control signals input from the control switches and the like provided on the front panel of this generator 121.

The operation of an ultrasonic operation system configured in this way is described next.

The surgical operator, prior to using the system, after connecting the generator plug 119 of the transmission cable 106 to the hand piece connector 126, connects the hand piece plug 103 to the drive signal plug 104 of the hand piece socket 105.

Additionally, when the hand switch unit 109 is used, the output plug 108 of the hand switch unit 109 is connected to the hand switch input plug 107, and the mounting piece 114 is connected to the connecting part 115 on the hand piece 101.

After such settings as these have been completed, when the system is to be used, the surgical operator depresses either the setting value output button 112 or the 100% output button 113 of the hand switch unit 110.

When the button is depressed, the switch detection circuit 124 detects which button was depressed and transmits a signal indicating the results of that detection to the control circuit 122. The control circuit 122, upon receiving that signal, adjusts the parameters to effect output corresponding to those detection results, and activates the drive circuit 123. Thereby, the drive circuit 123 generates and outputs a drive signal. When that drive signal is transmitted via the drive signal line 117 to the ultrasonic vibrator 116, the ultrasonic vibrator 116 generates ultrasonic vibrations, and those ultrasonic vibrations are transmitted via the ultrasonic vibration transmission unit to the hook-shaped operating member 102.

When the operating instrument being used is to be changed to another one, the treatment is performed as follows. The description given here assumes that the other operating instrument to be employed next does not use the hand switch unit 109.

First, the output plug 108 is removed from the hand switch input plug 107, and, at the same time, the hand piece plug 103 is removed from the drive signal plug 104 of the hand piece socket 105.

Then the hand piece plug 103 of the other operating instrument is connected to the drive signal plug 104 of the hand piece socket 105, in the same way as described earlier, and that other operating instrument can then be used.

At this time, the ultrasonic vibration output of the other operating instrument is turned on and off by manipulating the foot switch 129.

Based on such a third embodiment aspect as this, the hand switch unit can be freely attached to and detached from the cable that supplies the drive energy, wherefore it is possible to attach the hand switch unit only when needed, and also to select and use the optimal hand switch for each hand piece.

Accordingly, because the hand switches can be customized and formed in shapes that are optimal for each of the hand pieces, favorable operability can be realized.

When the hand switch is not needed, moreover, it can be removed, thus making it possible to prevent erroneous control inputs preemptively.

Figure 7:
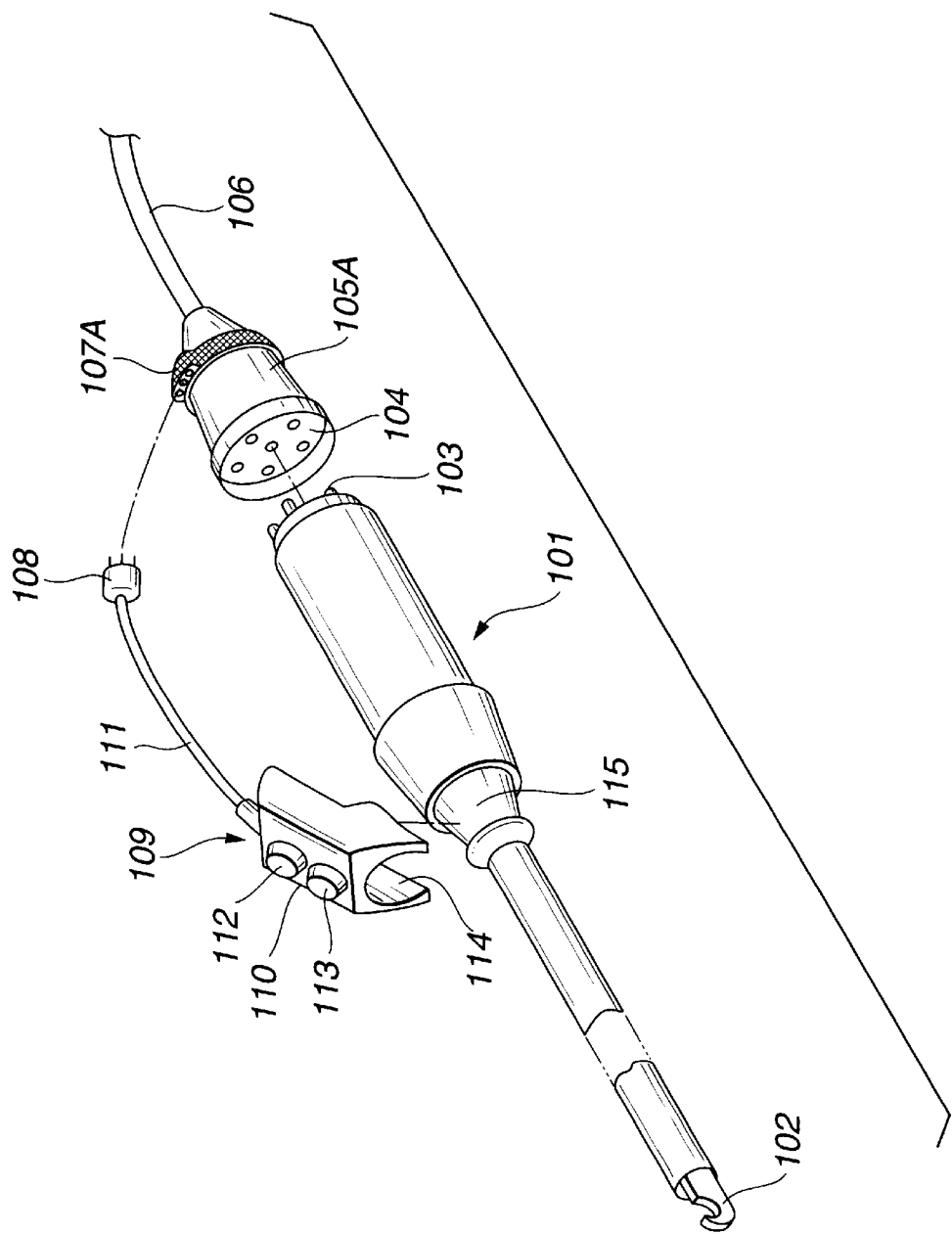
FIG. 7 is a diagonal view of the configuration of a hand piece and hand switch unit in an ultrasonic operation system in a fourth embodiment aspect of the present invention.

FIG. 7 shows a fourth embodiment aspect of the present invention. FIG. 7 is a diagonal view of the configuration of a hand piece and a hand switch unit in an ultrasonic operation system. In this fourth embodiment aspect, portions that are the same as in the third embodiment aspect are indicated by the same symbols and not further described here. Mainly the points of difference only are described.

The ultrasonic operation system in this fourth embodiment aspect is basically configured in the same way as the ultrasonic operation system in the third embodiment aspect, but with the following differences.

In the third embodiment aspect, the transmission cable 106 branches into two parts at the leading end thereof, with the hand piece socket 105 provided in one branching end 106*a*, and the hand switch input plug 107 provided in the other branching end 106*b*. In contrast therewith, in this fourth embodiment aspect, a hand switch input plug 107A is configured integrally in a hand piece socket 105A.

Described more particularly, the hand switch input plug 107A is configured so that it has a part for connecting with the output plug 108 protruding from the circumferential surface of the hand piece socket 105A that is roughly cylindrically shaped.

When an ultrasonic operation system having the hand piece socket 105A of such configuration as this is used, settings are made that are roughly the same as in the third embodiment aspect described earlier.

That is, the surgical operator, prior to using the system, after connecting the generator plug 119 of the transmission cable 106 to the hand piece connector 126, connects the hand piece plug 103 to the drive signal plug 104 of the hand piece socket 105A.

Additionally, when the hand switch unit 109 is to be used, the output plug 108 of the hand switch unit 109 is connected to the hand switch input plug 107A, and the mounting piece 114 is connected to the connecting part 115 on the hand piece 101.

Based on such a fourth embodiment aspect as this, while exhibiting roughly the same benefits as the third embodiment aspect, the output plug can be removed comparatively easily, because the hand switch input plug is secured on the hand piece socket, and it becomes possible to shorten surgical operation times.

Figure 8:
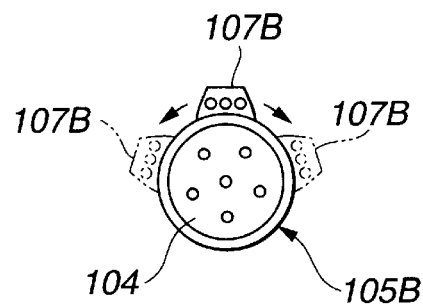
FIG. 8 is a front elevation of a hand piece socket and hand switch input plug in a fifth embodiment aspect of the present invention.

FIG. 8 shows a fifth embodiment aspect of the present invention. FIG. 8 is a front elevation representing the configuration of a hand piece socket and hand switch input plug. In this fifth embodiment aspect, portions that are the same as in the third or fourth embodiment aspects are indicated by the same symbols and not further described here. Mainly the points of difference only are described.

The ultrasonic operation system in this fifth embodiment aspect is basically configured in the same way as the ultrasonic operation system in the third embodiment aspect or fourth embodiment aspect, but with the following differences.

A hand switch input plug 107B is provided integrally on a hand piece socket 105B as described in the fourth embodiment aspect, but this hand switch input plug 107B in this fifth embodiment aspect is further configured so that it can be freely rotated along the circumferential surface of the hand piece socket 105B.

When an ultrasonic operation system having the hand piece socket 105B configured in this manner is used, settings are made that are roughly the same as in the fourth embodiment aspect described earlier.

Then, when the hand piece 101 is to be used, because the hand switch unit 109 is joined by fitting the mounting piece 114 onto the connecting part 115, as described earlier, the hand switch unit 110 can be rotated around the hand piece 101.

Thereupon, when the hand switch unit 110 is rotated to a desired position on the hand piece 101 according to the conditions wherein that hand piece 101 is being manipulated, the hand switch input plug 107B will rotate together with and so as to follow the rotation of the hand switch unit 109.

Based on such a fifth embodiment aspect as this, while realizing roughly the same benefits as in the third and fourth embodiment aspects described earlier, it becomes possible to adjust the hand switch attachment position as desired, wherefore operability is further enhanced. When the operating instrument has an odd shaped operating member such as a hook probe, for example, it is necessary that the surgical operator be able to set the hand switch attachment position according to his or her preference. That necessity can be met by the configuration described above.

Figure 9:
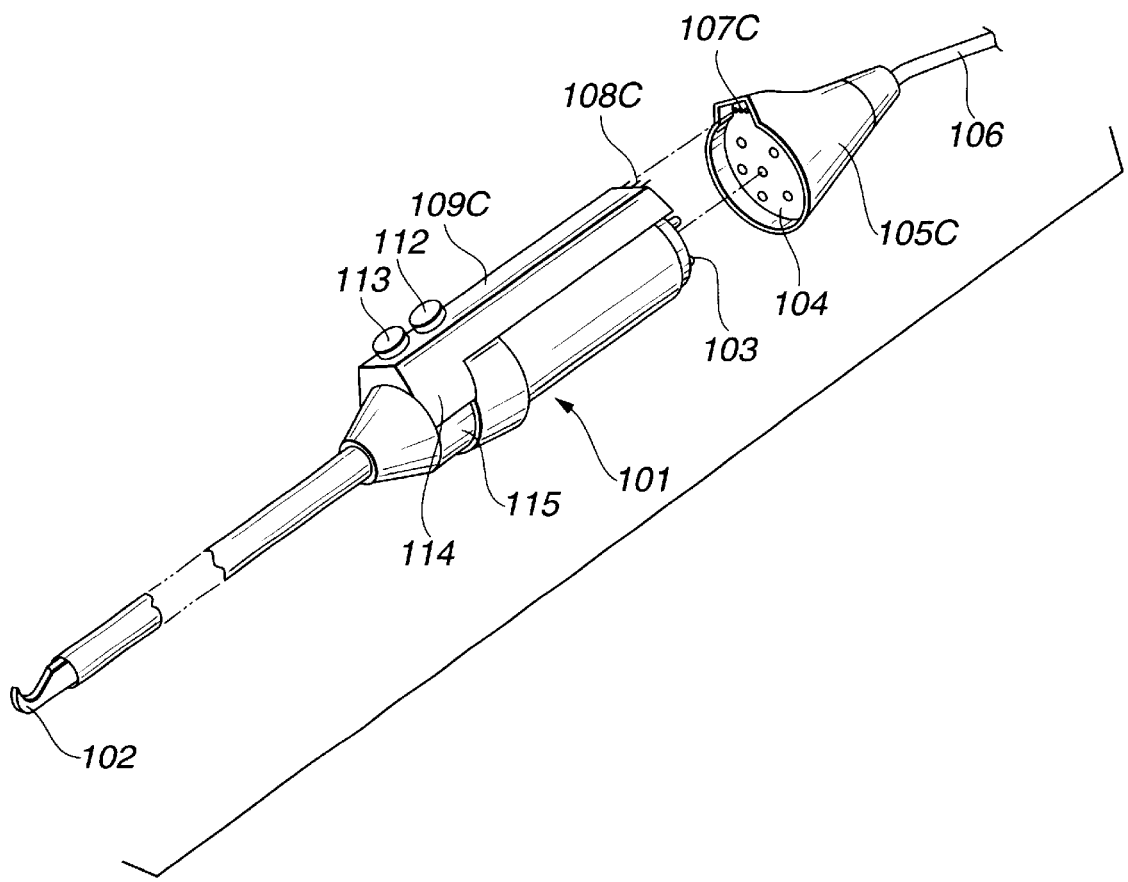
FIG. 9 is a diagonal view of the configuration of a hand piece and a hand switch unit in an ultrasonic operation system in a sixth embodiment aspect of the present invention.

In FIG. 9 is diagrammed a sixth embodiment aspect of the present invention. FIG. 9 is a diagonal view representing the configuration of a hand piece and hand switch unit in an ultrasonic operation system. In this sixth embodiment aspect, portions that are the same as in the third to fifth embodiment aspects are indicated by the same symbols and not further described here. Mainly the points of difference only are described.

The ultrasonic operation system in this sixth embodiment aspect is basically configured in the same way as the ultrasonic operation system in the third to fifth embodiment aspects, but with the following differences.

The hand switch unit 109C of this sixth embodiment aspect has the setting value output button 112, 100% output button 113, and mounting piece 114 described earlier, but the rear end of the main body thereof is extended to roughly the same position as the hand piece plug 103 of the hand piece 101, and there an output plug 108C is provided integrally.

A hand piece socket 105C provided at the leading end of the transmission cable 106, meanwhile, has the drive signal plug 104 and a hand switch input plug 107C provided on the same end surface, made so as to connect, respectively, to the hand piece plug 103 and the output plug 108C.

When an ultrasonic operation system having the hand switch unit 109C and hand piece socket 105C configured in this way is used, settings are made in the following manner.

The surgical operator, prior to using the system, connects the generator plug 119 of the transmission cable 106 to the hand piece connector 126, attaches the hand switch unit 109C to the hand piece 101, and then connects the hand piece plug 103 to the drive signal plug 104 of the hand piece socket 105C.

At this time, the output plug 108C and the hand switch input plug 107C do not have to be connected separately because they will naturally be connected simultaneously.

Moreover, when a hand piece of a type requiring no hand switch unit 109C is connected, only the hand piece plug 103 and the drive signal plug 104 of the hand piece socket 105C will be connected.

Moreover, if the hand switch unit 109C is custom formed according to the type and shape of the hand piece 101, operability will be enhanced in the same manner as already described.

Based on such a sixth embodiment aspect as this, while realizing roughly the same effects as in the third to fifth embodiment aspects described earlier, the hand switch will also be connected, simultaneously, when the hand piece socket is connected, rendering the setting operation simpler, and making it possible to shorten the operation time.

Figure 10:
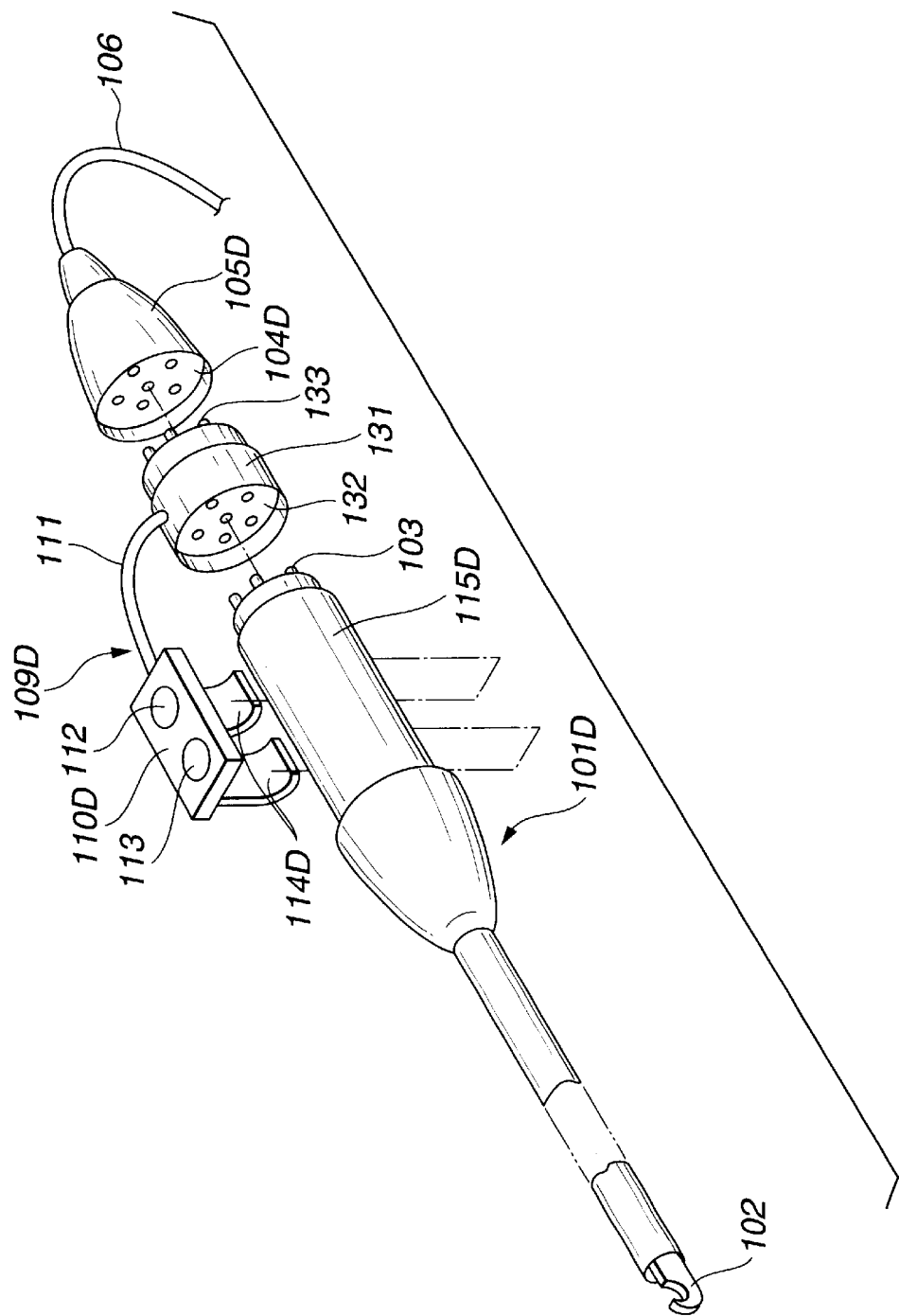
FIG. 10 is an exploded diagonal view of the configuration of a hand piece and a hand switch unit in an ultrasonic operation system in a seventh embodiment aspect of the present invention.
Figure 11:
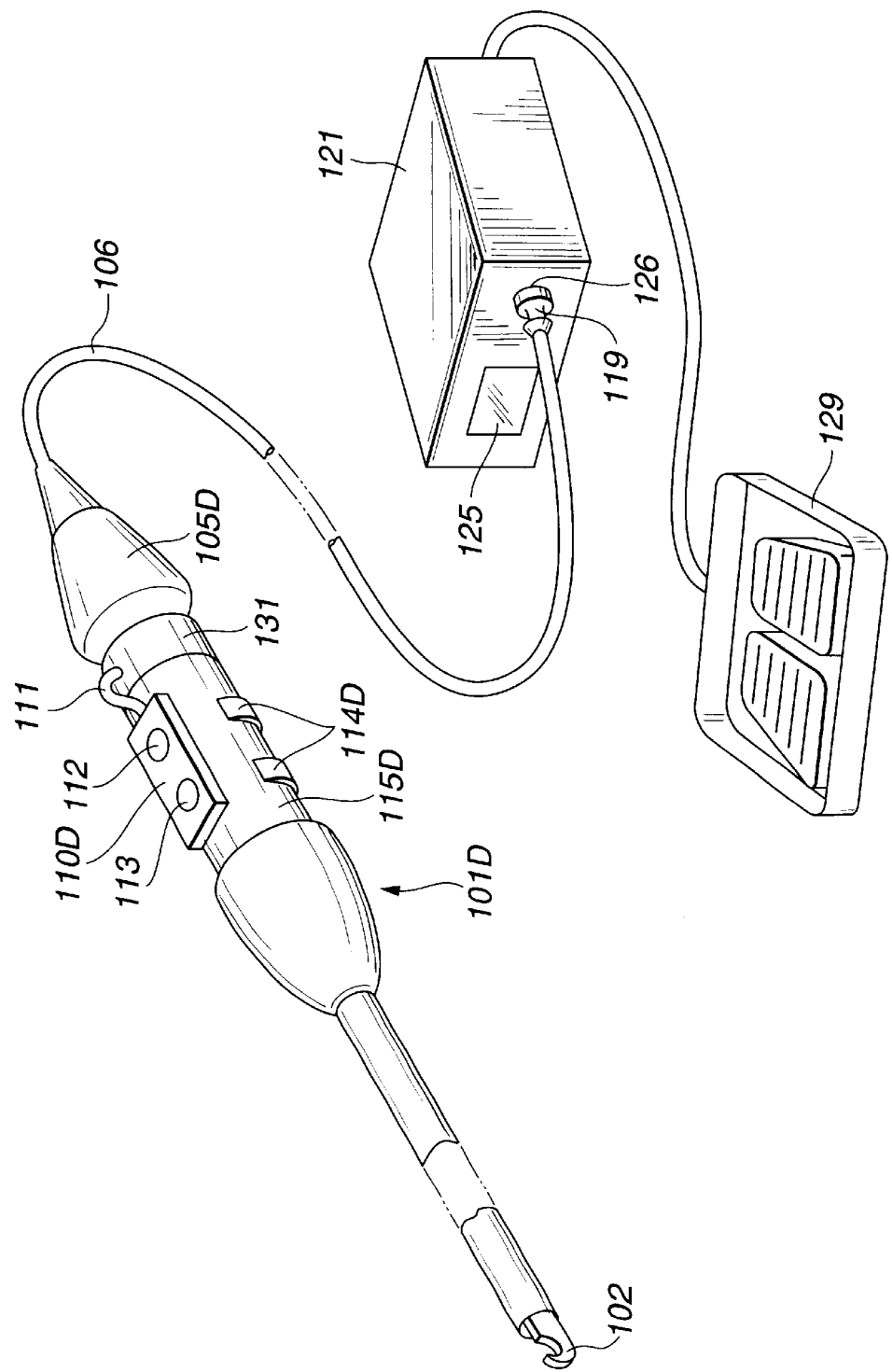
FIG. 11 is a diagonal view of the configuration of the ultrasonic operation system in the seventh embodiment aspect.
Figure 12:
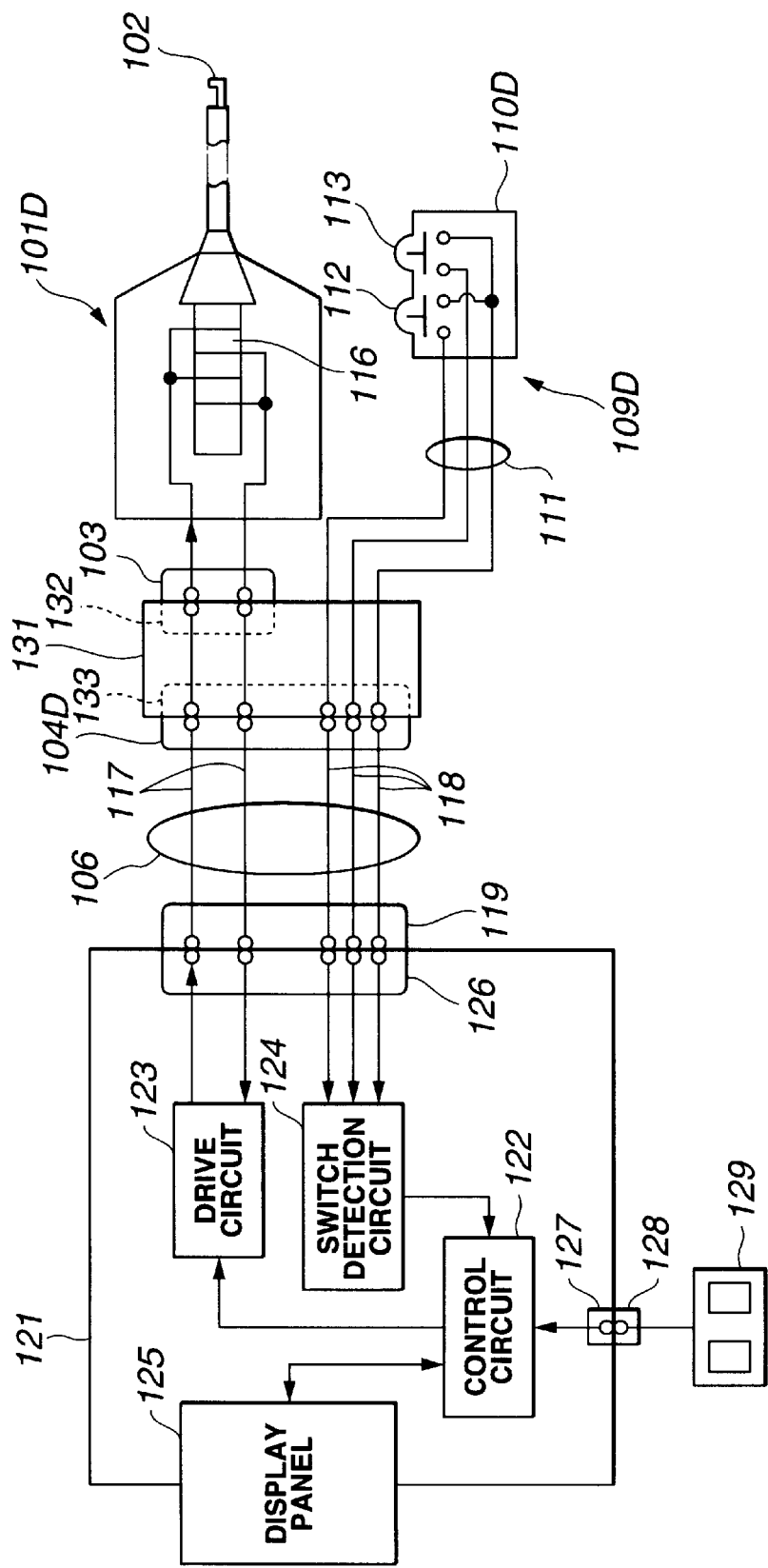
FIG. 12 is a diagram that uses blocks to represent parts of primarily the electrical configuration of the ultrasonic operation system in the seventh embodiment aspect.
Figure 13:
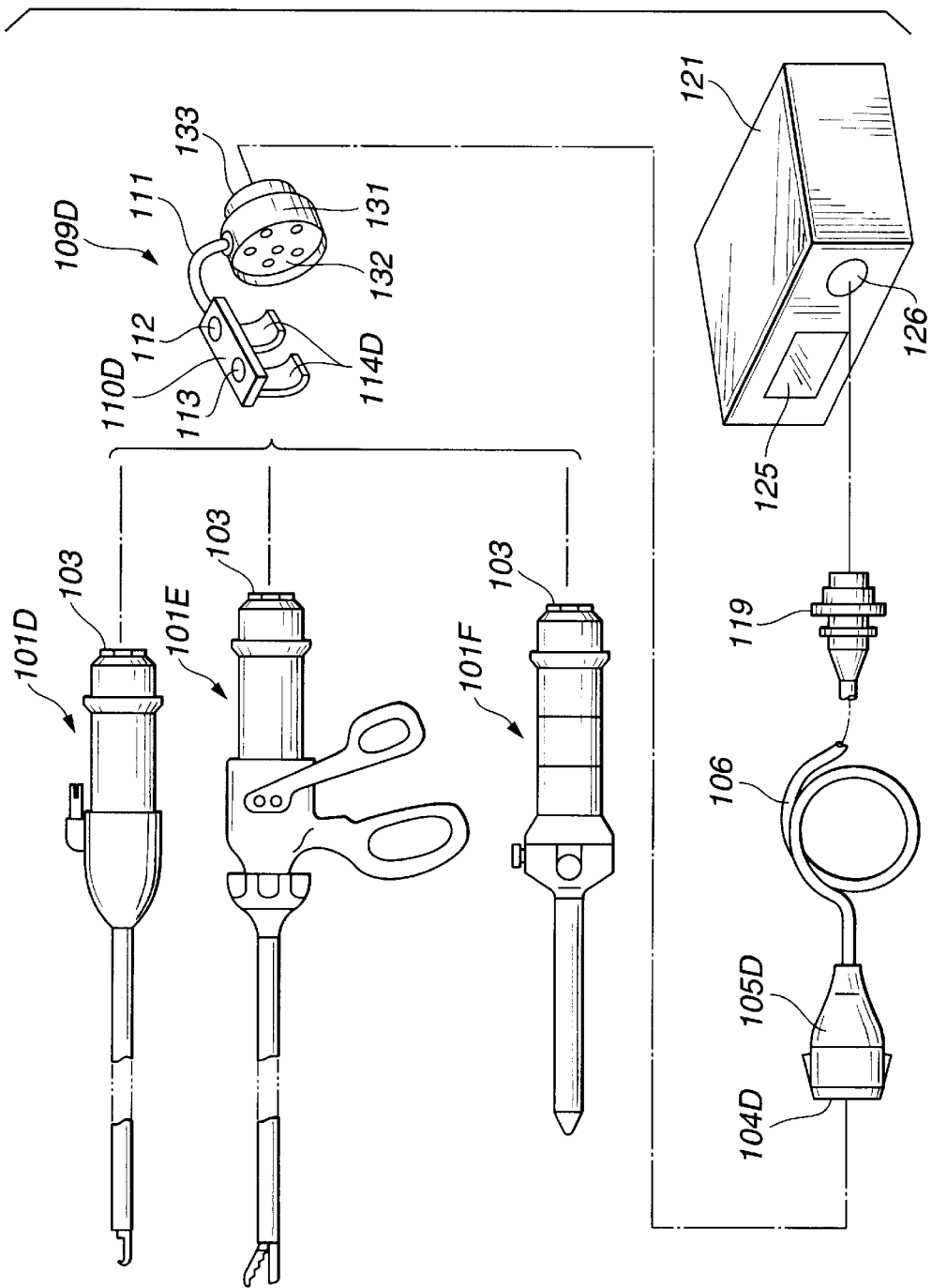
FIG. 13 is a diagram of combination examples in the ultrasonic operation system in the seventh embodiment aspect.

In FIGS. 10 to 13 is diagrammed a seventh embodiment aspect of the present invention. FIG. 10 is an exploded diagonal view of the configuration of a hand piece and a hand switch unit in an ultrasonic operation system, FIG. 11 is a diagonal view of the configuration of the ultrasonic operation system, FIG. 12 is a diagram that uses blocks to represent parts of primarily the electrical configuration of the ultrasonic operation system, and FIG. 13 is a diagram of combination examples in the ultrasonic operation system.

In this seventh embodiment aspect, portions that are the same as in the third to sixth embodiment aspects are indicated by the same symbols and not further described here. Mainly the points of difference only are described.

The hand piece 101D in this seventh embodiment aspect, differing from the hand piece 101 described earlier, is not provided with the dedicated connecting part 115, but, instead thereof, the grip part fulfills the functions of a connecting part 115D.

Furthermore, at the leading end of the transmission cable 106 is provided a hand piece socket 105D, and in that hand piece socket 105D is provided a common plug 104D constituting second connector means having a second energy signal output terminal and a first switching signal input terminal. In this common plug 104D are provided electrical contacts for carrying both drive signals and hand switch signals. This common plug 104D, described more particularly, in addition to comprising an array of electrical contacts capable of connecting the hand piece plug 103, having a third energy input terminal, by itself, is further provided with electrical contacts, additional to those electrical contacts, for carrying the hand switch signals, and so exhibits upward compatibility with the above-mentioned drive signal plug 104.

Provision is made so that, between such hand piece 101D and hand piece socket 105D, a hand switch unit 109D can be attached by a relay adapter 131 that constitutes a relay adapter unit.

This hand switch unit 109D comprises a hand switch component 110D that constitutes a hand switch relay and is the main switch unit for controlling output, mounting brackets 114D that project from the lower surface side of the hand switch component 110D and are for connecting to the connecting part 115D of the hand piece 101D, a hand switch cable 111 that is extended from the hand switch component 110D and is for carrying hand switch signals output from the hand switch component 110D, and the relay adapter 131 noted above, provided at the rear end of this hand switch cable 111.

The hand switch component 110D is provided with the setting value output button 112 and the 100% output button 113.

The relay adapter 131 is configured so as to connect to the hand piece plug 103, and so as to have a drive signal plug 132 constituting fourth connector means having a third energy signal output terminal for transmitting drive signals, and a common plug 133, constituting a fourth connector receptacle having a second energy signal input terminal for inputting drive signals and a first switching signal output terminal for outputting hand switch signals, which connects with the common plug 104D.

In FIG. 11 is diagrammed a condition wherein the hand piece 101D, hand switch unit 109D, and hand piece socket 105D, such as described in the foregoing, are mutually connected, and set connected to the generator 121 to which the foot switch 129 has been connected.

Next, with reference to FIG. 12, a description is given of the circuit configuration of an ultrasonic operation system comprising a hand piece 101D such as is described in the foregoing and the generator 121.

The electrical configuration of the hand piece 101D, the electrical configuration of the hand switch component 110D of the hand switch unit 109D, and the configuration of the generator 121 and foot switch 129 and so forth are the same as indicated earlier in reference to FIG. 6.

The common plug 104D provided at one end of the transmission cable 106, as noted above, is provided with an electrical contact that is connected to the drive signal line 117 and with an electrical contact that is connected to the hand switch signal line 118. The generator plug 119 provided at the other end of the transmission cable 106 is the same as described above.

The relay adapter 131 of the hand switch unit 109D, furthermore, as noted above, is provided with the drive signal plug 132 that is connected to the hand piece plug 103 and transmits drive signals, and the common plug 133 that is connected to the common plug 104D and transmits drive signals and hand switch signals.

When an ultrasonic operation system having the hand switch unit 109D, hand piece 101D, and hand piece socket 105D configured in this way is used, settings are made as follows.

The surgical operator, before using the system, first connects the generator plug 119 of the transmission cable 106 to the hand piece connector 126 and also connects the hand piece plug 103 to the drive signal plug 132 of the relay adapter 131, and then attaches the hand switch unit 109D to the hand piece 101D by fitting the mounting brackets 114D onto the connecting part 115D.

Subsequently, the common plug 133 of the hand switch unit 109D made integral with the hand piece 101D is connected to the common plug 104 of the hand piece socket 105D.

When connecting to a hand piece of a type not requiring the hand switch unit 109D, the hand piece plug 103 of the hand piece 101D and the common plug 104D of the hand piece socket 105D will be connected directly. As described earlier, the common plug 104D is upward compatible with the drive signal plug 104, wherefore such direct connection is possible.

In FIG. 13 are diagrammed ultrasonic operation system combination examples wherein the hand switch unit 109D such as is described in the foregoing is used.

The hand switch unit 109D is made so that it can be used not only in combinations with the hook probe type hand piece 101D as noted above, but also in combinations with a scissors type hand piece 101E or trocar probe type hand piece 101F.

The hand pieces 101D, 101E, and 101F are made so as to have a common hand piece plug 103. When the hand switch unit 109D is attached to any one of those hand pieces 101D, 101E, and 101F, that is done by connecting that hand piece plug 103 to the drive signal plug 132 of the relay adapter 131, and connecting the common plug 133 to the common plug 104D of the hand piece socket 105D.

When any one of the hand pieces 101D, 101E, and 101F is to be used without attaching the hand switch unit 109D, the hand piece plug 103 is connected directly to the common plug 104D of the hand piece socket 105D.

Thus, by connecting the relay adapter 131 between the hand piece socket 105D and one of the plurality of types of hand pieces, namely 101D, 101E, and 101F, so that it is sandwiched therebetween, a system is configured wherein the hand switch unit 109D can be used.

The hand switch unit 109D may also be custom formed according to the type or shape of the hand piece. In this case, operability is further improved, as already noted.

Based on such a seventh embodiment aspect as this, roughly the same effects are realized as in the third to sixth embodiment aspects described earlier and, when the hand switch is not to be used, the hand switch unit can be removed, resulting in a compact condition with no hand switch input plug or the like. Thus operability can be enhanced whether the surgical operator is one who prefers a foot switch or one who prefers a hand switch.

In the description given in the foregoing, ultrasonic operation systems employing ultrasonic vibrations are exemplified as energy operating systems for performing treatments on living tissue. However, the invention is not limited thereto or thereby, and configurations wherein similar hand switch units are attached can be applied to systems using other treatment energy.

Figure 14:
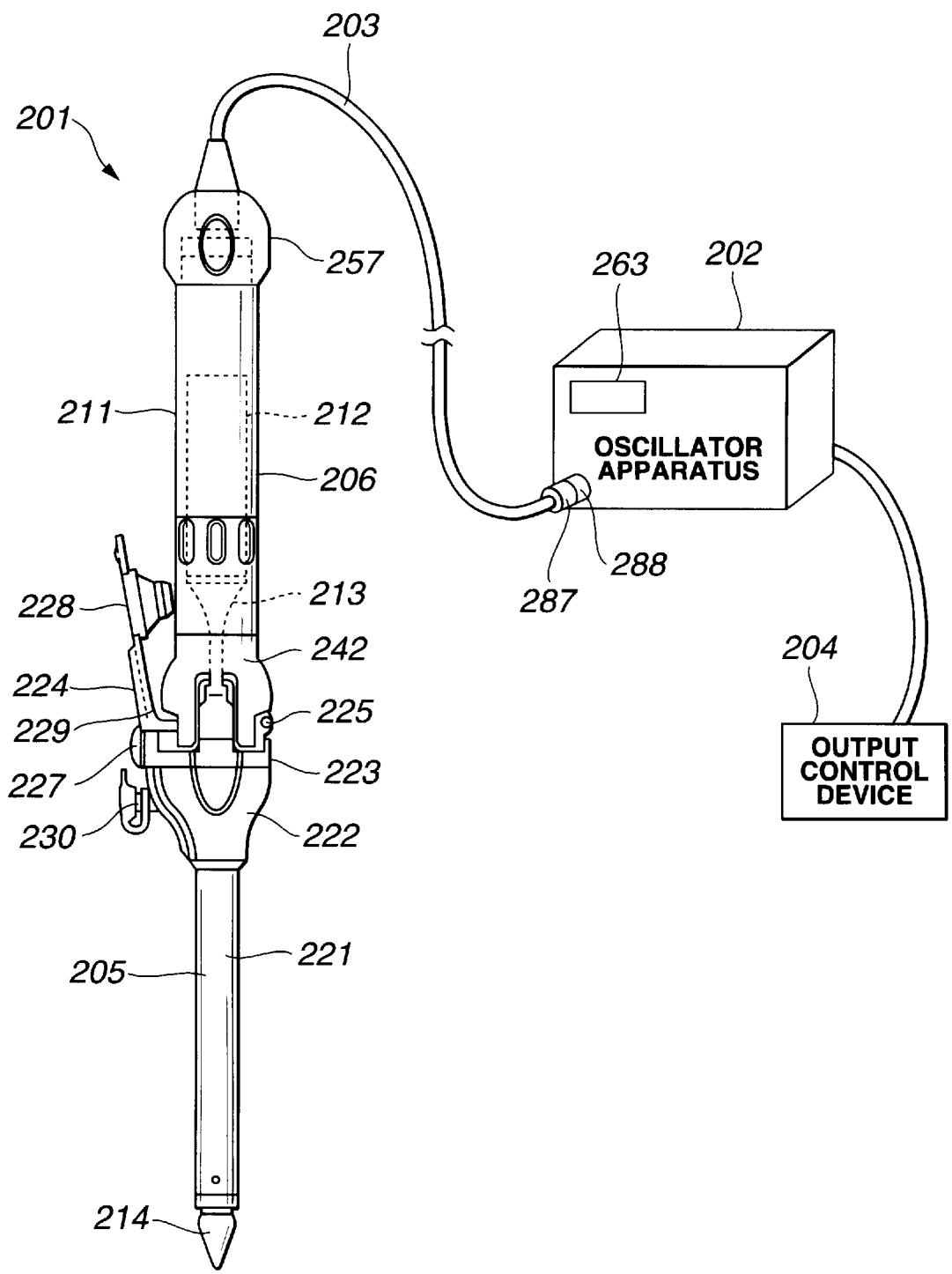
FIG. 14 is a diagram that shows how connections are made in an ultrasonic operation system in an eighth embodiment aspect of the present invention.
Figure 15:
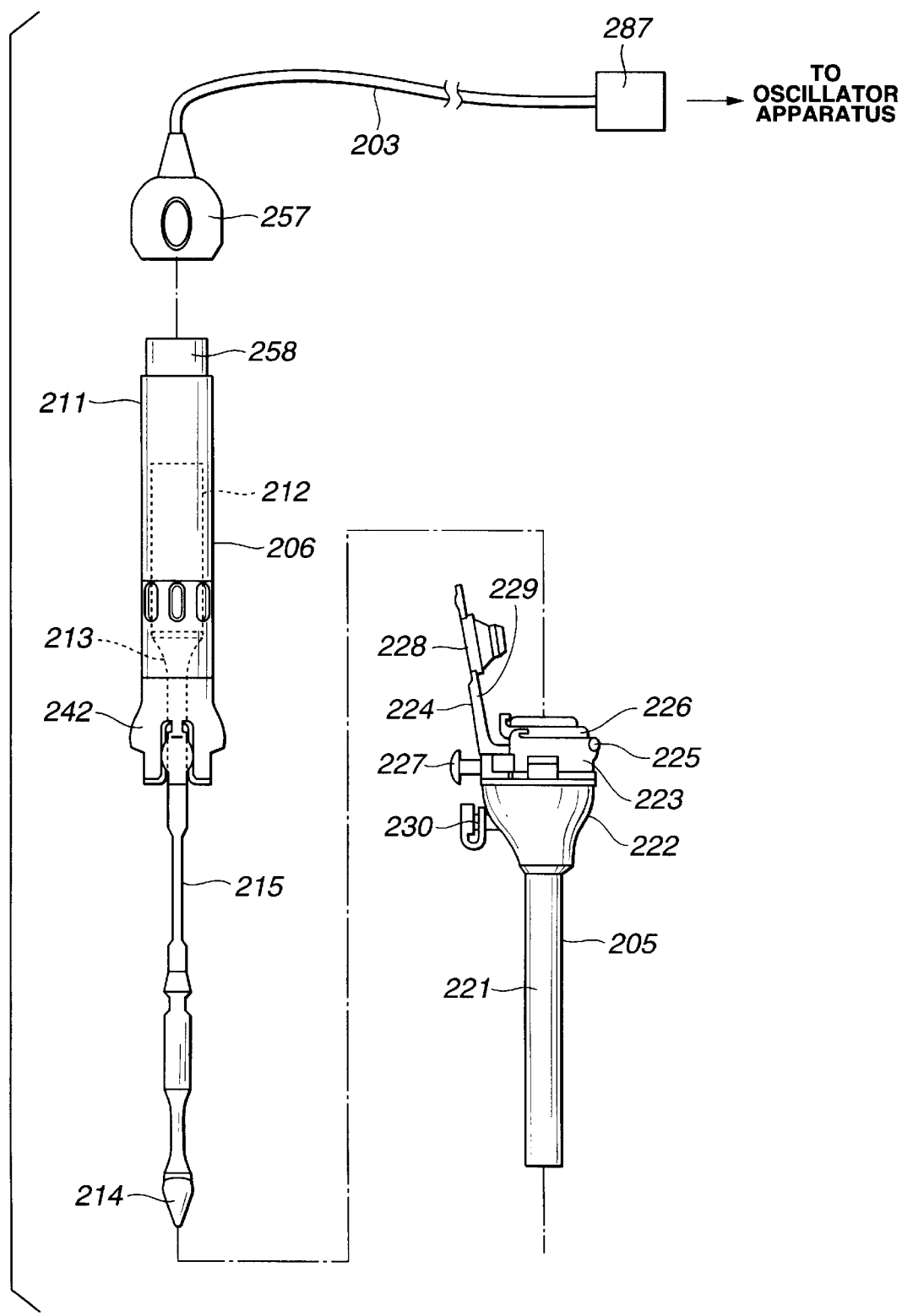
FIG. 15 is a diagram that shows the disassembled ultrasonic operation system in the eighth embodiment aspect.
Figure 16:
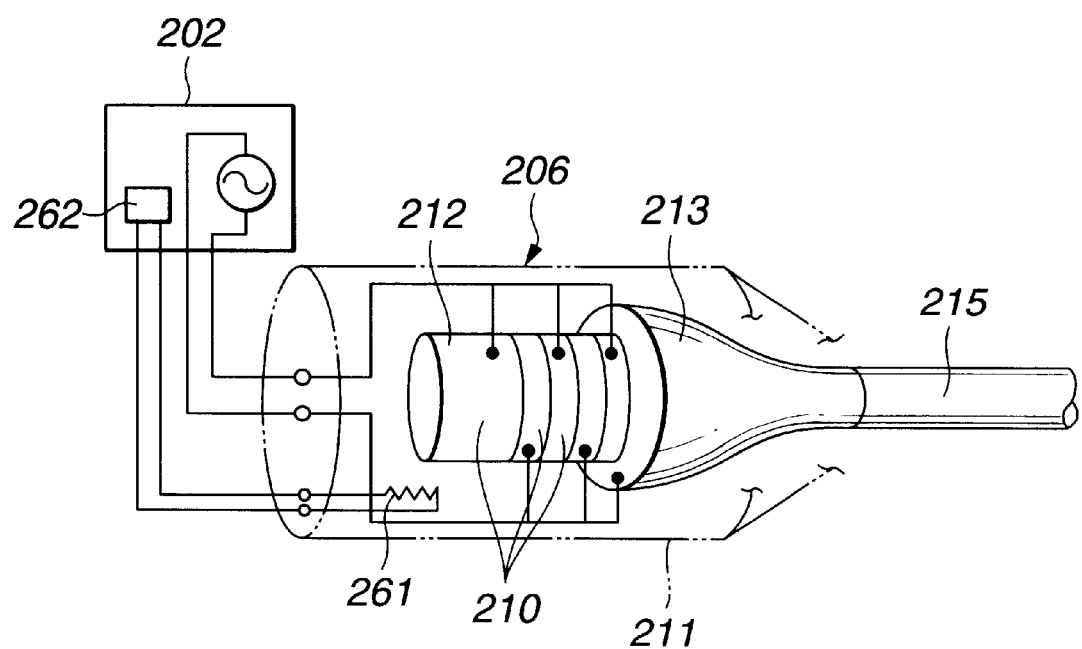
FIG. 16 is a simplified diagram of the configuration of a hand piece in the ultrasonic operation system in the eighth embodiment aspect.
Figure 17A:
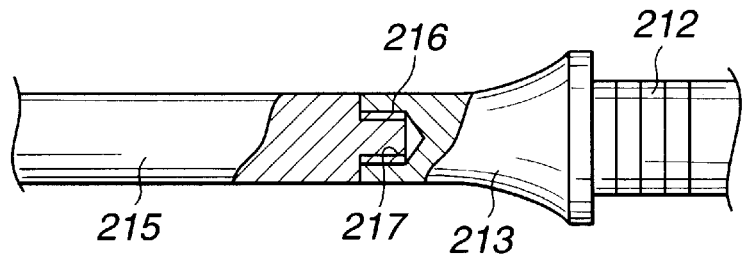
FIG. 17A is a diagram of a first configuration example wherein a horn and an ultrasonic vibration transmission member are fixedly coupled and made integral in the ultrasonic operation system in the eighth embodiment aspect.
Figure 17B:
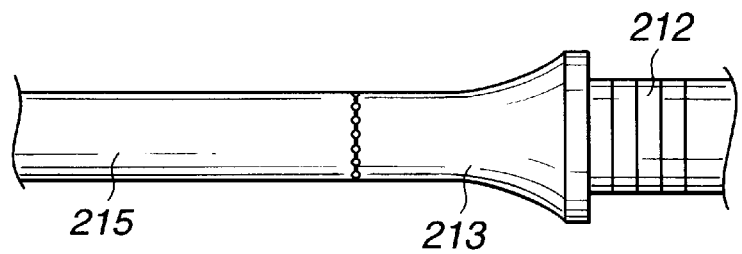
FIG. 17B is a diagram of a second configuration example wherein a horn and an ultrasonic vibration transmission member are fixedly coupled and made integral in the ultrasonic operation system in the eighth embodiment aspect.
Figure 17C:
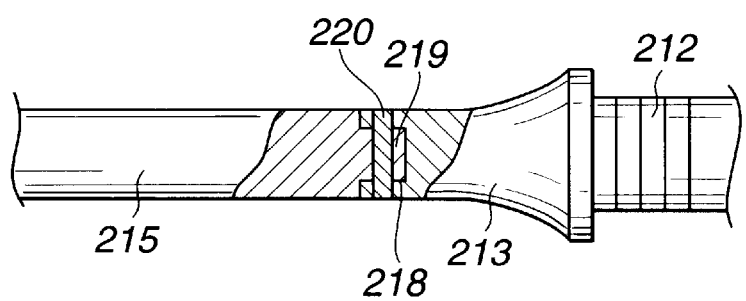
FIG. 17C is a diagram of a third configuration example wherein a horn and an ultrasonic vibration transmission member are fixedly coupled and made integral in the ultrasonic operation system in the eighth embodiment aspect.
Figure 17D:
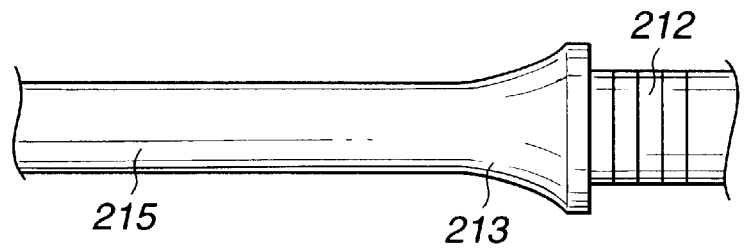
FIG. 17D is a diagram of a fourth configuration example wherein a horn and an ultrasonic vibration transmission member are fixedly coupled and made integral in the ultrasonic operation system in the eighth embodiment aspect.
Figure 18:
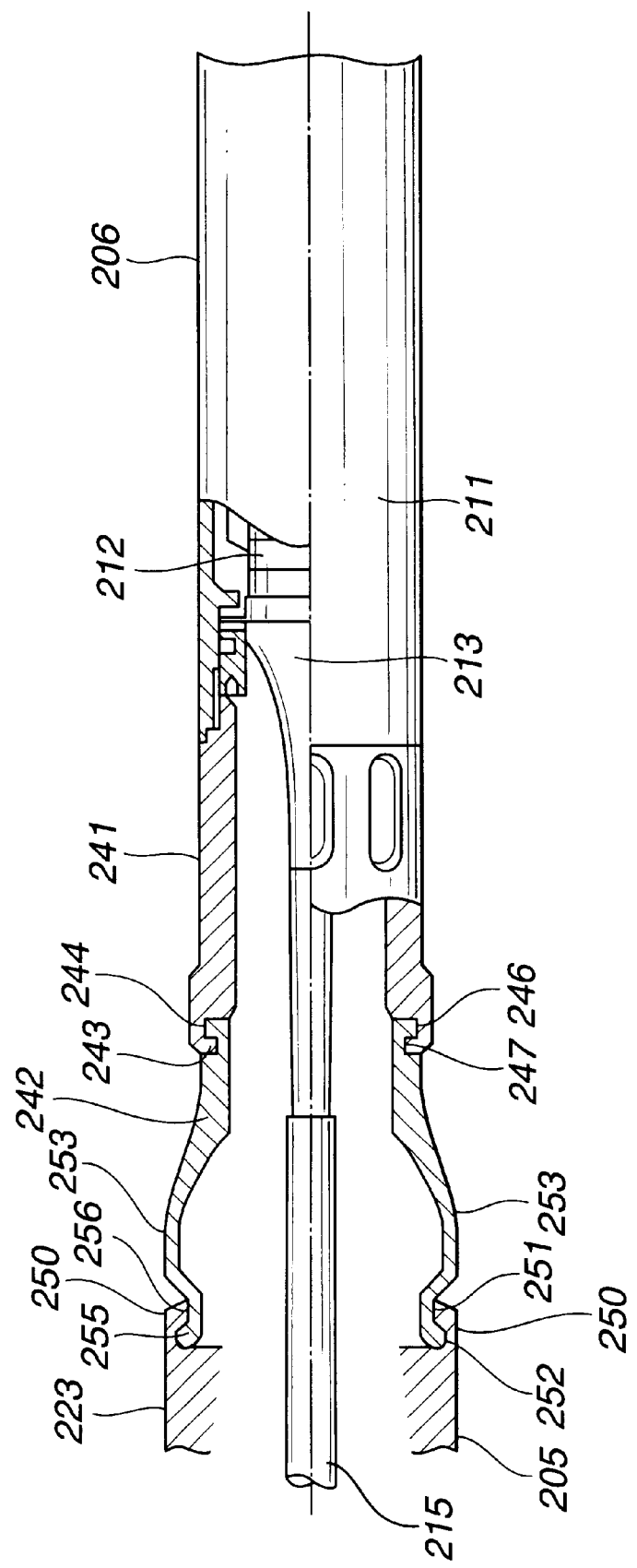
FIG. 18 is a side elevation that represents, partially in cross-section, a structure for detachably connecting an outer cannula and a hand piece in the ultrasonic operation system of the eighth embodiment aspect.
Figure 19:
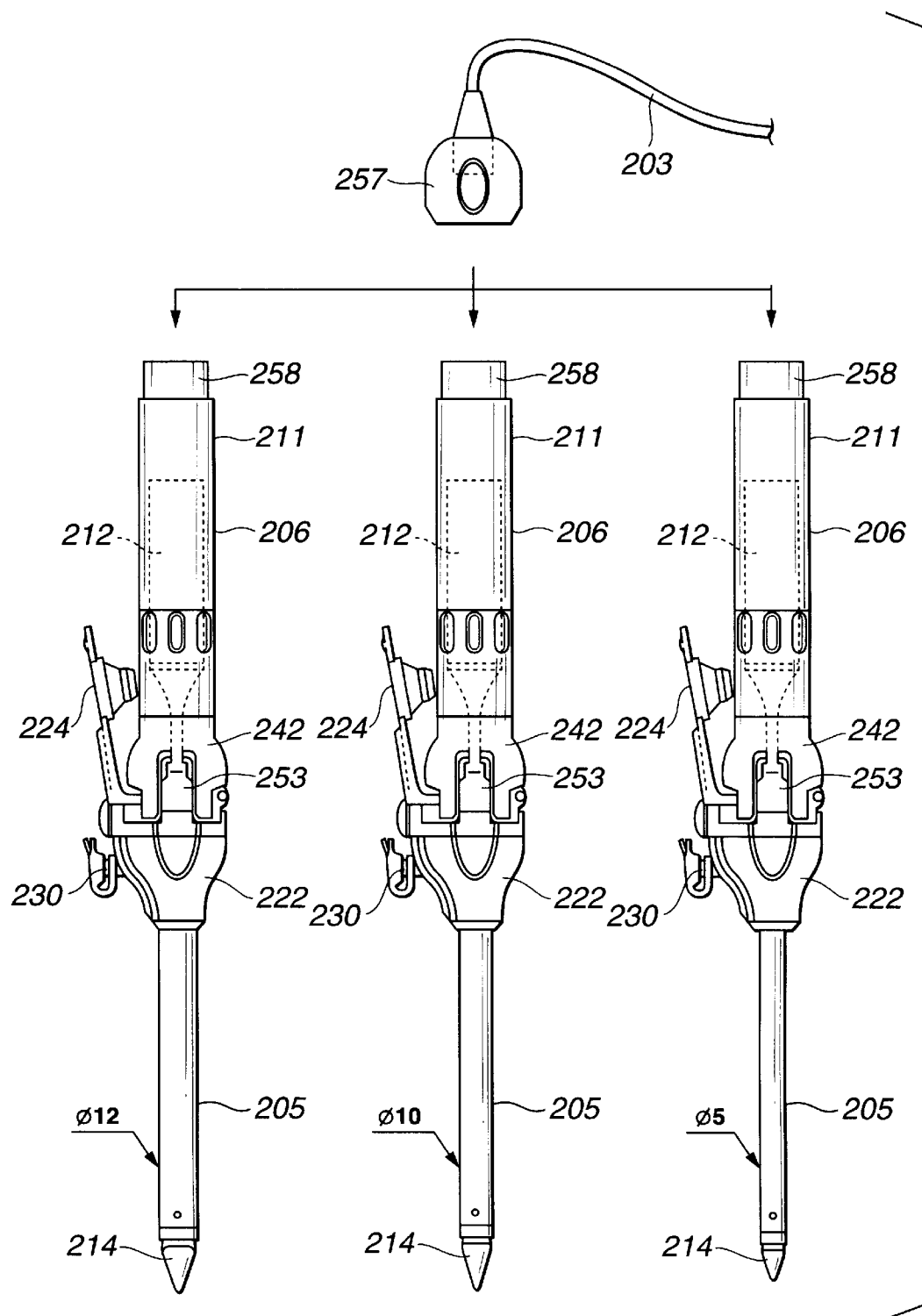
FIG. 19 is a diagram that shows how it is possible to connect a common cable to a plurality of hand pieces in the ultrasonic operation system in the eighth embodiment aspect.
Figure 20:
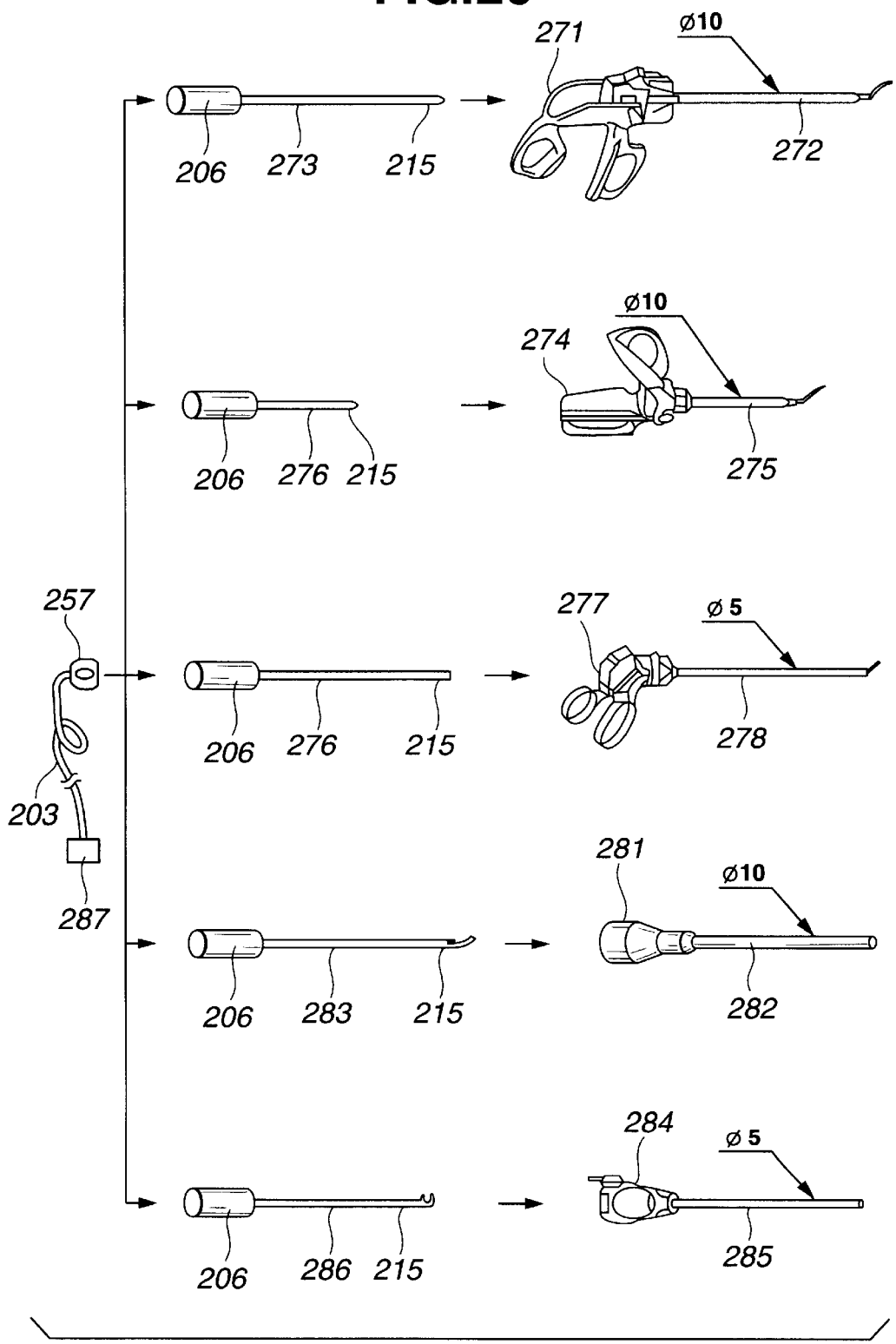
FIG. 20 is a diagram that shows how it is possible to connect a common cable to a plurality of hand pieces connected to a plurality of operating instruments in the ultrasonic operation system in the eighth embodiment aspect.
Figure 21:
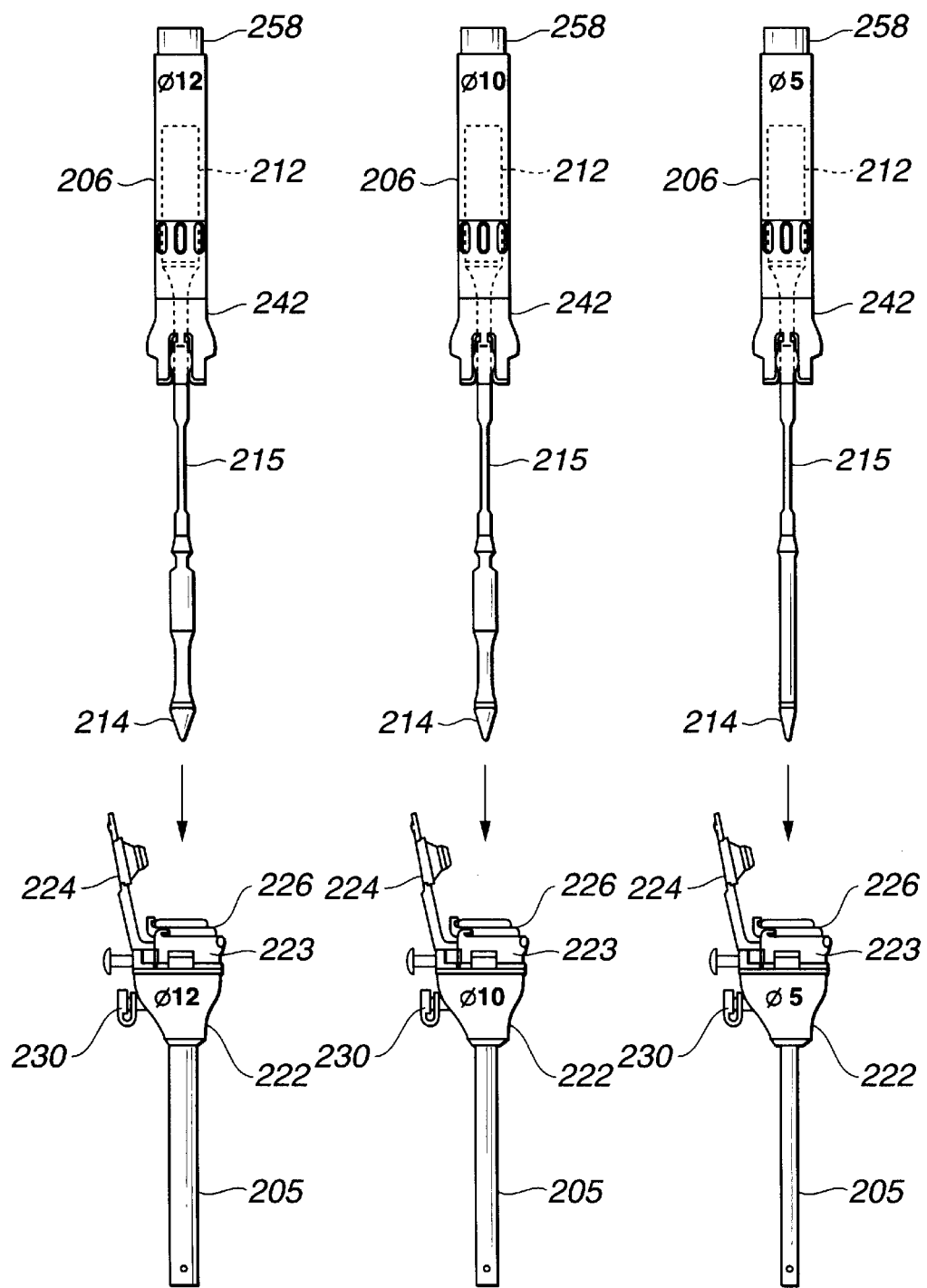
FIG. 21 is a diagram representing examples where identification means are provided in a plurality of hand pieces and in the outer cannulas corresponding thereto in the ultrasonic operation system in the eighth embodiment aspect.

In FIGS. 14 to 21 is diagrammed an eighth embodiment aspect of the present invention. FIG. 14 is a diagram that shows how connections are made in an ultrasonic operation system in an eighth embodiment aspect of the present invention, FIG. 15 is a diagram that shows the ultrasonic operation system disassembled, FIG. 16 is a simplified diagram of the configuration of a hand piece in the ultrasonic operation system, FIG. 17A is a diagram of a first configuration example wherein a horn and an ultrasonic vibration transmission member are fixedly coupled and made integral in the ultrasonic operation system, FIG. 17B is a diagram of a second configuration example wherein a horn and an ultrasonic vibration transmission member are fixedly coupled and made integral in the ultrasonic operation system, FIG. 17C is a diagram of a third configuration example wherein a horn and an ultrasonic vibration transmission member are fixedly coupled and made integral in the ultrasonic operation system, FIG. 17D is a diagram of a fourth configuration example wherein a horn and an ultrasonic vibration transmission member are fixedly coupled and made integral in the ultrasonic operation system, FIG. 18 is a side elevation that represents, partially in cross-section, a structure for detachably connecting an outer cannula and a hand piece in the ultrasonic operation system, FIG. 19 is a diagram that shows how it is possible to connect a common cable to a plurality of hand pieces in the ultrasonic operation system, FIG. 20 is a diagram that shows how it is possible to connect a common cable to a plurality of hand pieces connected to a plurality of operating instruments in the ultrasonic operation system, and FIG. 21 is a diagram representing examples where identification means are provided in a plurality of hand pieces and in the outer cannulas corresponding thereto in the ultrasonic operation system.

This ultrasonic operation system is configured, as diagrammed in FIG. 14, with an ultrasonic operation apparatus 201 connected via a cable 203 to an oscillator apparatus 202 that functions as an output generation apparatus, and an output control device 204 such as a foot switch for controlling output operations connected to the oscillator apparatus 202.

The ultrasonic operation apparatus 201 in this eighth embodiment aspect relates to an example where an ultrasonic trocar is configured as the operating instrument. When not being used, it is disassembled into various parts, as diagrammed in FIG. 15, namely an outer cannula 205, a hand piece 206 equipped with a probe mounted detachably to that outer cannula 205, and the cable 203 for supplying electrical drive power, detachably mounted to that hand piece 206.

When such an ultrasonic operation apparatus 201 is used, it may be assembled to realize the condition diagrammed in FIG. 14 by inserting an ultrasonic vibration transmission member (probe) 215 (such as diagrammed in FIG. 15) of the hand piece 206 into the outer cannula 205, thus joining that outer cannula 205 and hand piece 206, and then connecting the cable 203 to the hand piece 206.

The hand piece 206 has an ultrasonic vibrator 212 mounted inside a cylindrical case 211, and, as diagrammed in FIG. 16, the ultrasonic vibration transmission member 215 having an operating member 214 at the leading end thereof is fixedly connected to a horn 213 in the ultrasonic vibrator 212. This ultrasonic vibration transmission member 215 receives ultrasonic vibrations generated by the ultrasonic vibrator 212 from the horn 213 and transmits them to the operating member 214.

The ultrasonic vibrator 212, as diagrammed in FIG. 16, is configured with a plurality of piezoelectric elements 210 in a stack, such that ultrasonic vibrations are generated when a drive voltage is applied through electrodes. The ultrasonic vibrations so generated are amplified by the horn 213 so that their amplitude increases.

As described in the foregoing, the ultrasonic vibration transmission member 215 is coupled fixedly to the horn 213 of the ultrasonic vibrator 212. These ultrasonic vibration transmission member 215 and horn 213 constitute a structure wherein they cannot be attached or detached when being used normally, and are handled as a single entity.

As to the means for fixedly coupling the ultrasonic vibration transmission member 215 and the horn 213 of the ultrasonic vibrator 212, those diagrammed in FIGS. 17A to 17D, for example, are conceivable.

What are diagrammed in FIGS. 17A to 17C are examples of means for integrally configuring the horn 213 and the ultrasonic vibration transmission member 215, those being separate members, by fixedly coupling those members.

First, in the first configuration example diagrammed in FIG. 17A, female threads 216 are formed in the leading end of the horn 213, male threads 217 are formed in the base end of the ultrasonic vibration transmission member 215, the male threads 217 are screwed into the female threads 216, and the screwed in portions and the end surfaces constituting joining surfaces are bonded together with an adhesive, thereby integrally fixing the horn 213 and the ultrasonic vibration transmission member 215. Thus, in this example, provision is made so that the horn 213 and the ultrasonic vibration transmission member 215 are fixedly coupled and made integral by the use of screw fastening and bonding.

The adhesive used in this case should be one that is highly heat-resistant so as to withstand the environment wherein the hand piece 206 is used. In the description above, moreover, the female threads are provided in the horn 213 and the male threads 217 are provided in the ultrasonic vibration transmission member 215, but this may of course be reversed so that the male threads 217 are provided in the horn 213 and the female threads 216 are provided in the ultrasonic vibration transmission member 215.

Next, the second configuration example diagrammed in FIG. 17B is one wherein the leading end of the horn 213 and the base end of the ultrasonic vibration transmission member 215 are fixedly coupled and made integral by either welding or brazing.

Next, the third configuration example diagrammed in FIG. 17C is one wherein the horn 213 and the ultrasonic vibration transmission member 215 are fixedly coupled and made integral by first forming a hole 218 in the leading end of the horn 213 and forming a projection 219 in the base end of the ultrasonic vibration transmission member 215, then inserting and fitting the projection 219 into the hole 218, and finally passing a pin 220 commonly through the hole 218 and the projection 219.

While the pin 220 is used here to effect integration after the fitting together, that poses no limitation, and integration may be effected by using an adhesive to bond together the portions that fit together and the end surfaces that constitute the joining surfaces. Needless to say, moreover, instead of forming the hole 218 in the horn 213 and the projection 219 in the ultrasonic vibration transmission member 215, the projection 219 may be formed in the horn 213, and the hole 218 formed in the ultrasonic vibration transmission member 215.

The fourth configuration example diagrammed in FIG. 17D, on the other hand, is one wherein the horn 213 and the ultrasonic vibration transmission member 215 are formed of a single member, and thereby fixedly coupled and made integral.

Means for fixedly coupling the horn 213 and the ultrasonic vibration transmission member 215 so that they cannot be attached or detached are not limited to the examples described in the above. Even if the configuration is one wherein the horn 213 and the ultrasonic vibration transmission member 215 are coupled by being screwed together, as conventionally, it is only necessary, in addition thereto, to provide means to prevent attachment and detachment so that a user cannot remove the ultrasonic vibration transmission member 215 from the horn 213. One conceivable specific example of such attachment/detachment prevention means would be a structure or the like wherein the portion where a tool is brought to bear when the ultrasonic vibration transmission member 215 is screw-coupled is covered so that it cannot be seen by a user.

The outer cannula 205 mounted to the hand piece 206 is configured as follows.

The outer cannula 205 is configured so as to have a sheath 221 having an internal tubular passage, and a holder unit 222 that is connected at the base end of the sheath 221 and has space formed therein which communicates with the tubular passage in the sheath 221. In the holder unit 222, on one side thereof, is provided a mouth fitting 230 that communicates with the tubular passage of the sheath 221.

In the opening at the base end of the holder unit 222, a cap 223 is provided, and in this cap 223 are provided a push button 227 and a flap valve (not shown) that is opened and closed by the push button 227.

The flap valve is configured so that it is usually in a position that closes the opening at the base end of the holder unit 222 due to a spring (not shown), and so that, when a trocar needle or the hand piece 206 is mounted, the push button 227 is pushed in, and turns, withdrawing toward the space provided inside the holder unit 222, thus opening the opening at the base end of that holder unit 222.

Furthermore, to the cap 223 is detachably mounted a seal member 224. This seal member 224 is configured so as to have a base end part that is held at the position of the opening at the base end of the holder unit 222, an arm member 229 extended diagonally from that base end part, and a valve member 228 formed at the tip end of that arm member 229. In the base end part thereof is formed a first seal hole, and in the valve member 228 is formed a second seal hole having a smaller diameter than the first seal hole.

The base end part of the seal member 224, to describe it more particularly, is attached by being held sandwiched between the cap 223 and a seal securing member 226 provided in that cap 223 such that it can freely turn on a shaft 225. Accordingly, this seal member 224 is configured so that it can be removed from the cap 223 by turning the seal securing member 226.

In the cap 223 provided in the holder unit 222 of the outer cannula 205, furthermore, connection means are provided for detachably connecting the hand piece 206. These connection means are configured as diagrammed in FIG. 18, for example.

First, to the leading end of case 211 of the hand piece 206, a cylindrical connection member 241 is connected and fixed by screw fastening or the like so that it becomes coaxial with that case 211.

Also, to the leading end of the connection member 241, a connection ring 242 is connected so that it becomes coaxial with the connection member 241 and so that it can turn freely relative to that connection member 241.

In other words, in the inner surface of the leading end of the connection member 241 are formed a projection 243 and a groove 244 that extend all the way around the circumference, while in the outer surface of the base end of the connection ring 242 are formed a projection 246 and a groove 247 that extend all the way around the circumference, so that, by mutually reversing the concave-convex relationship, the projection 243 and groove 244, and also the groove 247 and projection 246, respectively interlock.

Accordingly, it is possible for the connection ring 242 to turn concentrically with the connection member 241. At such time, the parts joined with the projection 243 and the groove 247 and the parts joined with the groove 244 and the projection 246 are interlocked so that they generate friction forces that counteract the turning force, so that the two cannot be turned by a slight force, resulting in a configuration wherein, in order to effect turning, a conscious turning action must be performed, bringing to bear a commensurately strong force.

The outer cannula 205 described earlier is coupled with this connection ring 242 that can turn freely in this manner.

That is, in the cap 223 of the outer cannula 205, a pair, for example, of claw-shaped receiving pieces 250 are provided, extended toward the base end direction, and a projection 251 and groove 252 are formed in the inner surfaces of those receiving pieces 250.

Also, at the leading end of the connection ring 242, a pair of latching arms (latching pawls) 253 are provided that project forward after bulging to the outside, corresponding to the pair of receiving pieces 250. At the outer surfaces of these latching arms 253 are formed grooves 256 and projections 255 for meshing with the projections 251 and the grooves 252 in the receiving pieces 250 so that the concave-convex relationship is reversed.

By such a configuration as this, when the hand piece 206 is mounted to the outer cannula 205, the latching arms 253 are deformed, flexing to the inside, and the projections 251 of the receiving pieces 250 and the projections 255 of the latching arms 253 mutually ride up over each other and interlock to effect latching.

When removing the hand piece 206 from the outer cannula 205, the latching arms 253 are depressed with the fingers or the like, deforming those latching arms 253 so that they flex to the inside, thereby releasing the interlocking of the projections 251 of the receiving pieces 250 and the projections 255 of the latching arms 253. Then, with that interlocking so released, by pulling out the hand piece 206 toward the front, the hand piece 206 can be removed from the outer cannula 205.

In the aft end of the hand piece 206, an electrical connection unit 258 is provided for detachably connecting a connector 257 provided in the leading end of the cable 203.

This electrical connection unit 258 has a common configuration irrespective of the type of the hand piece 206 of the ultrasonic operation apparatus 201. Thus, whether the ultrasonic operation apparatus 201 has the same types of hand pieces 206 or different types of hand pieces 206, they can be connected to the connector 257 of the common cable 203.

Thus, by commonly using the cable 203, left connected as is to the oscillator apparatus 202 via a connector 287 at the other end, as diagrammed in FIG. 14, a plurality of hand pieces 206 can be connected, and, for that reason, there is no need to have a separate cable 203 available for each hand piece 206 that is used.

A description is now given, with reference to FIG. 19, of a configuration wherein multiple hand pieces 206 that are of the same model but different specifications are selectively connected to the same cable 203.

Every one of the plurality of ultrasonic trocars diagrammed in FIG. 19 is configured roughly in the same way as the one described above, but the diameters of the outer cannula 205 are different, being φ5, φ10, and φ12, respectively (where the symbol "φ" represents the diameter in mm units), constituting ultrasonic operation apparatuses 201 when combined with that which is compatible with the outer cannula 205. Each of these ultrasonic operation apparatuses 201 is configured so that the connector 257 of the cable 203 can be commonly connected.

In FIG. 20 is represented a relationship wherein the connector 257 of the cable 203 can be connected commonly to a plurality of ultrasonic operation apparatuses 201, inclusively of different models, together with the relationship of operating instruments that are combined with the vibrator units.

At the top in FIG. 20 are diagrammed an operating instrument 271 configured as scissors with an insertion part 272 having a diameter of φ10, and a vibrator unit 273 used in that operating instrument 271.

Second from the top in FIG. 20 are diagrammed an operating instrument 274 configured as short scissors with an insertion part 275 having the same diameter of φ10, and a vibrator unit 276 used in that operating instrument 274.

In the middle in FIG. 20 are diagrammed an operating instrument 277 configured as scissors with an insertion part 278 having a diameter of φ5, and a vibrator unit 279 used in that operating instrument 277.

Second from the bottom in FIG. 20 are diagrammed an operating instrument 281 configured as a hook with an insertion part 282 having a diameter of φ10, and a vibrator unit 283 used in that operating instrument 281.

And at the bottom in FIG. 20 are diagrammed an operating instrument 284 configured as a hook with an insertion part 285 having a diameter of φ5, and a vibrator unit 286 used in that operating instrument 284.

The connector 257 of the cable 203 is made so that it can be commonly connected to any of the vibrator units 273, 276, 279, 283, and 286 used respectively in the operating instruments 271, 274, 277, 281, and 284.

Thus provision is made so that the common cable 203 can be connected to the vibrator unit used in any of the operating instruments, whether they be operating instruments of the same type but different scheme as diagrammed in FIG. 19 or operating instruments of different type as diagrammed in FIG. 20.

Also, as described in the foregoing, in each of the operating instruments 271, 274, 277, 281, and 284 is used the corresponding vibrator unit 273, 276, 279, 283, or 286, respectively, but, when that is done, it is preferable that identification means (discrimination means) be added in order to clarify the relationships between compatible pairs. An example of such identification means that may be mentioned include the application of an indication to both members of mutually compatible combinations, wherewith the fact of their being a combination can be distinguished, such as a common color, common letters or characters, common symbol, or common number, for example.

In FIG. 21 are diagrammed examples of an ultrasonic trocar that is one example of an operating instrument wherein such identification means as these are provided. There are three outer cannulas 205 having respectively different diameters of φ12, φ10, and φ5, respectively, and ultrasonic vibrator units for the hand piece 206 wherein are provided ultrasonic vibration transmission members 215 that are compatible with those outer cannulas 205, on both members of which combinations are applied the correspondingly common characters "φ12," "φ10," and "φ5," respectively.

Now, in the oscillator apparatus 202, one socket 288 for connecting the connector 287 of the cable 203 is generally provided, as diagrammed in FIG. 14, but this poses no limitation, and it is possible to provide a plurality of sockets 288. When a plurality of sockets 288 is provided, it will of course be possible to employ a plural number of cables 203. When the number of cables 203 is large, however, there is a possibility of the work being thereby interfered with, wherefore it is preferable to make provision so that, if at all possible, a fewer number of cables 203 is connected and used than the number of operating instruments being used.

Also, in each of the hand pieces 206 is incorporated some discrimination means for identifying itself. The discrimination means in this eighth embodiment aspect are made such that, as diagrammed in FIG. 16, a resistor element 261 is incorporated inside the hand piece 206, the resistance value of that resistor element 261 is read out by a detection circuit 262 incorporated in the oscillator apparatus 202, via an identification signal transmission line, and, according to that detected resistance value, the type of the hand piece 206 wherein that resistor element 261 is incorporated, that is, the vibrator unit integrated with the probe, is distinguished. In Table 1 are represented examples of associations between the resistance value of the resistor element 261 and the hand piece type.

TABLE 1

| Resistance | Hand Piece Type |
| --- | --- |
| 50 Ω | φ 5 hand piece |
| 100 Ω | φ10 hand piece |
| 200 Ω | φ12 hand piece |

As indicated in Table 1 above, the φ5 hand piece is distinguished when the resistance value is 50 Ω, the φ10 hand piece is distinguished when the resistance value is 100 Ω, and the φ12 hand piece is distinguished when the resistance value is 200 Ω.

At the oscillator apparatus 202 which has recognized which type the vibrator unit is by such discrimination means as this, at least one of the frequency, voltage, and current is controlled so that the power supplied to the recognized vibrator unit will be suitable.

In the oscillator apparatus 202, furthermore, the number of times that vibrator unit was used, the frequency when used, the voltage when used, and the current used, etc., are stored in memory as data. Then, based on those stored data, the usage level of the vibrator unit is computed. Those usage level data can be displayed on a display device 263 provided in the oscillator apparatus 202, but provision is made so that, when the usable life of the vibrator unit recognized is nearly elapsed, that fact is notified ahead of time by a warning display or audible alarm or the like.

Based on such an eighth embodiment aspect as this, provision is made so that the cable 203 is used in common for a plurality of sets of outer cannulas 205 and hand pieces 206 wherein compatible members are combined, wherefore the cable 203 connected as is to the oscillator apparatus 202 can be used, and a plurality of cables 203 is not needed.

Furthermore, because the cable 203 connected as is to the oscillator apparatus 202 can be used commonly with a plurality of ultrasonic operation apparatuses 201, not only is the need to provide multiple cables for each of the multiple ultrasonic operation apparatuses 201 eliminated, but the task of connecting the hand piece 206 and the cable 203 can be done immediately on the user's end, without having to ask an assistant to connect the oscillator apparatus 202 and the cable 203, which makes handling easier and facilitates better work efficiency.

Also, because the hand piece 206 and the ultrasonic vibration transmission member 215 are coupled integrally and fixedly, there is no need to assemble these every time the ultrasonic operation apparatus 201 is used, nor will mistakes in assembly be made. Thus it becomes possible to use the apparatus quickly and work efficiency is improved. Furthermore, because of the integral structure wherewith there is no danger of screwing pieces together too tightly or not tightly enough, an efficient ultrasonic operation apparatus 201 is realized that exhibits good ultrasonic transmission performance, stable operating conditions, and little heat generation.

Also, because the outer cannula 205 and the hand piece 206 that is detachably mounted to that outer cannula 205 can be axially rotated relatively to each other, the orientation of the ultrasonic vibration transmission member 215 and the operating member 214 can be changed to facilitate operating ease without changing the gripping condition.

Moreover, because the resistor element 261 is incorporated as identification means in the hand piece 206, it becomes possible to accurately ascertain and monitor the usage level and remaining life of the ultrasonic vibration transmission member 215 that comprises the operating member 214. Because the durability performance of the ultrasonic vibration transmission member 215 is poorer than that of the hand piece 206, so that the ultrasonic vibration transmission member 215 will wear out earlier, such a configuration as this is extremely effective.

Figure 22:
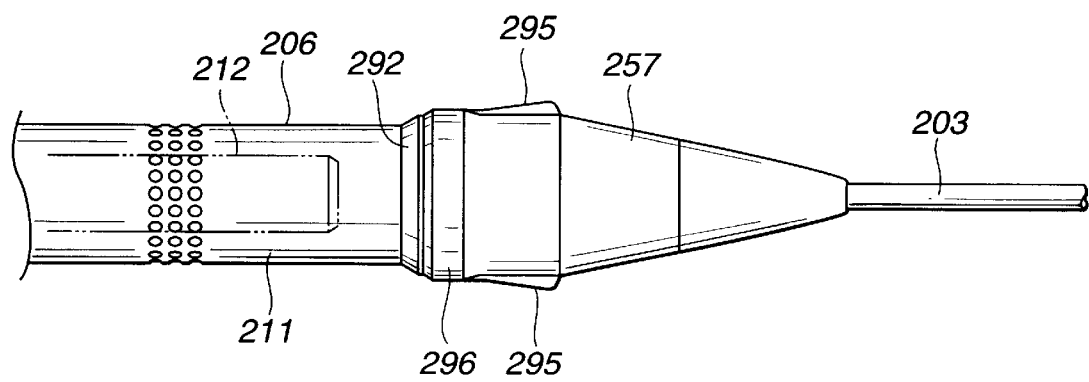
FIG. 22 is a side elevation that shows how a cable connector is connected to a hand piece in an ultrasonic operation system in a ninth embodiment aspect of the present invention.
Figure 24A:
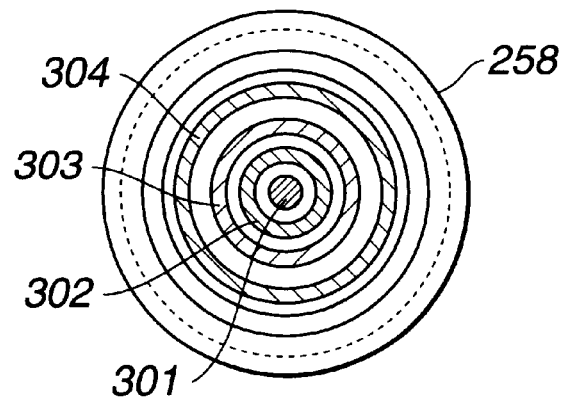
FIG. 24A is an end surface view that represents the structure of an electrical connecting unit for a hand piece in the ultrasonic operation system in the ninth embodiment aspect.
Figure 24B:
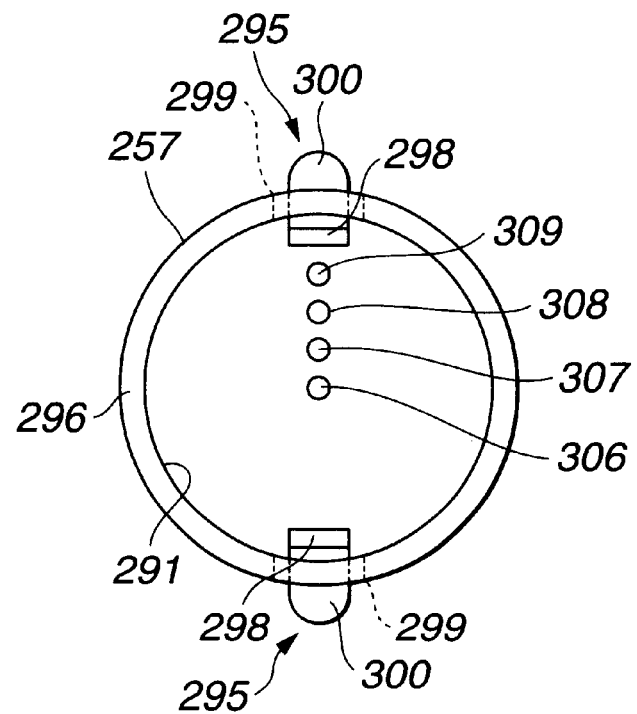
FIG. 24B is an end surface view that represents the structure of a cable connector in the ultrasonic operation system in the ninth embodiment aspect.

In FIGS. 22 to 24B is diagrammed a ninth embodiment aspect of the present invention. FIG. 22 is a side elevation that shows how a cable connector is connected to a hand piece in an ultrasonic operation system, FIG. 23 is a side elevation that represents, partially in cross-section, a connection structure for a hand piece and a cable connector in the ultrasonic operation system, in its disassembled condition, FIG. 24A is an end surface view that represents the structure of an electrical connecting unit for a hand piece in the ultrasonic operation system, and FIG. 24B is an end surface view that represents the structure of a cable connector in the ultrasonic operation system.

In this ninth embodiment aspect, portions that are the same as in the eighth embodiment aspect are indicated by the same symbols and not further described here. Mainly the points of difference only are described.

In the eighth embodiment aspect described in the foregoing, provision was made so that the connector 257 of the common cable 203 could be connected to the electrical connection unit 258 of the hand piece 206 of the ultrasonic operation apparatus 201. In this ninth embodiment aspect, however, provision is further made so that it is possible to connect the connector 257 of the cable 203 to the electrical connection unit 258 of the hand piece 206 so that it can be turned about the axis of the cable 203.

The electrical connection unit 258 of the hand piece 206 diagrammed in FIG. 23 is formed so that the outer circumference exhibits a cylindrical surface shape. By mounting the connector 257 of the cable 203 to that outer circumference so that it is fit over it, as diagrammed in FIG. 22, the hand piece 206 and the cable 203 are coupled in a turnable condition.

That is, the connector 257 has a cylindrical connection member 291 formed which fits over the outer circumference of the electrical connection unit 258, and that cylindrical connection member 291 is provided with an inner circumferential shape that makes it possible to fit tightly onto the outer circumference of the electrical connection unit 258 such that it (i.e. the cylindrical connection member 291) can turn.

At the extreme end of this electrical connection unit 258 is formed a positioning collar 292 against which the leading end of the cylindrical connection member 291 abuts when the cylindrical connection member 291 is mated and connected.

Moreover, slightly on the inside of the circumferential edge in the leading end surface of the electrical connection unit 258, a ring-shaped inner groove 293 is formed that extends all the way around the circumference thereof, and, on the wall surface on the outer circumferential side of that inner groove 293, a ring-shaped latching projection 294 is formed that extends all the way around the circumference.

In the cylindrical connection member 291, meanwhile, are provided pawls 295 for latching to the latching projection 294.

These pawls 295 are configured so that they have a ring member 296 secured to the outer circumference of the leading end of the cylindrical connection member 291, and flexible pieces 297 extended from that ring member 296 toward the back. These flexible pieces 297, after being extended toward the back, are first bent inward, in the inner radial direction, and then bent forward, and at the extreme ends thereof are formed latching projections 298 for latching the latching projection 294. In these flexible pieces 297, the intermediate portions thereof extending toward the back are formed as bulging portions 300 that stick out to the outside of the cylindrical connection member 291 such as diagrammed in FIGS. 22 and 23, in a configuration wherein these bulging portions 300 can be pressed in with the fingers from the outside of the cylindrical connection member 291.

The pawls 295 such as these ordinarily press in toward the inside of the cylindrical connection member 291 through cutouts 299 formed in the cylindrical connection member 291.

First, to connect the hand piece 206 and the connector 257, the following procedure is performed.

When the cylindrical connection member 291 of the connector 257 is plugged into the electrical connection unit 258 of the hand piece 206 so that it mates, the latching projections 298 of the pawls 295 bite into the inner groove 293, and ride up over the latching projection 294, whereupon a mutual latching condition like that indicated by the double-dotted line in FIG. 23 is realized. Thus the connector 257 is latched and connected to the electrical connection unit 258 of the hand piece 206, and a condition is attained wherein the hand piece 206 and the connector 257 are connected such that they can freely turn, about their axes, relative to each other.

Next, to remove the hand piece 206 from the connector 257, the following procedure is performed.

The bulging portions 300 of the flexible pieces 297 are pushed in by the fingers from the outside of the cylindrical connection member 291, and thereby the latching projections 298 of the pawls 295 are released from the latching projection 294. By pulling out the connector 257, in this condition, that connector 257 can be removed from the hand piece 206.

Next, the electrically connecting structure of the hand piece 206 and the connector 257 is described with reference to FIGS. 24A and 24B.

In the end surface of the electrical connection unit 258 of the hand piece 206, as diagrammed in FIG. 24A, are provided a first electrode 301 formed as a point positioned at the center axis, a second electrode 302 formed in a ring shape about the outer circumference of the first electrode 301, a third electrode 303 formed in a ring shape about the outer circumference of the second electrode 302, and a fourth electrode 304 formed in a ring shape about the outer circumference of the third electrode 303, the last three mentioned whereof being thus formed concentrically about the center axis.

In the end surface of the connector 257, meanwhile, are deployed a first electrode 306, a second electrode 307, a third electrode 308, and a fourth electrode 309, each being in a contact pin shape, at positions corresponding respectively to the first electrode 301, second electrode 302, third electrode 303, and fourth electrode 304.

In such a configuration as this, when the connector 257 is mounted to the electrical connection unit 258 of the hand piece 206, the first, second, third, and fourth electrodes 306, 307, 308, and 309 on the connector 257 side individually contact, and are electrically connected to, the first, second, third, and fourth electrodes 301, 302, 303, and 304 on the hand piece 206 side, respectively. This condition of being electrically connected is maintained even when the connector 257 and hand piece 206 are turned relatively to each other as described earlier.

Provision is made so that, in such a connected condition as this, the combination of the first electrodes 301 and 306 and the combination of the second electrodes 302 and 307 are used for supplying drive power to the ultrasonic vibrator 212, while the combination of the third electrodes 303 and 308 and the combination of the fourth electrodes 304 and 309 are used for transmitting signals of the resistor element 261 that constitutes discrimination means.

Based on such a ninth embodiment aspect as this, in addition to exhibiting roughly the same benefits as the eighth embodiment aspect described earlier, because the hand piece 206 can turn freely with respect to the connector 257 of the cord 3, the cord 3 can be prevented from twisting when the hand piece 206 is being used, thus eliminating that problem.

Also, because the cord 3 will not become twisted even when the hand piece 206 is manipulated so as to turn, the hand piece 206 can be lightly manipulated so as to turn.

Furthermore, because the hand piece 206 can freely turn relative to the outer cannula 205, the hand piece 206 can be made to assume various forms without having to be forced, and the operability of the hand piece 206 are enhanced.

In this invention, it is apparent that various modifications in a wide range can be made on this basis of this invention without departing from the spirit and scope of the invention. This invention is not restricted by any specific embodiment except being limited by the appended claims.

What is claimed is:

1. An ultrasonic operation system comprising:
   a plurality of handpieces each having an ultrasonic transducer for generating ultrasonic vibrations, a case for housing the ultrasonic transducer and a probe for transmitting the ultrasonic vibrations to a living tissue;
   a drive signal generator unit including a drive signal generator circuit for generating drive signals for driving the ultrasonic transducer;
   a transmission cable having a distal end and a proximal end for transmitting the drive signals;
   a first connector device comprising a first plug provided at the proximal end of the transmission cable and a receptacle provided to the drive signal generator unit, the first plug and the receptacle being removably connected to each other; and
   a second connector device comprising a plurality of second plugs including electrodes exposed from a rear end of each of the plurality of handpieces and a socket provided at the distal end of the transmission cable, at lest one of the plurality of second plugs being selectively and removably attached to the socket so as to share the transmission cable.

2. The ultrasonic operation system according to claim 1, wherein the socket has a recess to receive at least one of the plurality of second plugs, and output terminals for outputting the drive signals transmitted via the transmission cable, the output terminals being located at positions to transmit the drive signals to the electrodes in the recess when at least one of the plurality of second plugs is received in the recess.

3. The ultrasonic operation system according to claim 1, wherein at least one of the plurality of handpieces is configured such that the probe can be removed from the ultrasonic transducer to be replaced with a different type of probe.

4. The ultrasonic operation system according to claim 1, further comprising a switch assembly including a main switch unit which is removably mounted to at least one of the plurality of handpieces and which generates an operating signal for operating a predetermined function of the ultrasonic operation system and an operation signal output part for outputting the operating signal generated by the main switch unit.

5. The ultrasonic operation system according to claim 4, wherein the drive signal generator unit further comprises a control circuit for controlling the drive signal generator circuit in accordance with the operating signal.

6. The ultrasonic operation system according to claim 4, wherein the operating signal output part is an output plug including one or more operating signal output terminals for outputting the operating signals.

7. The ultrasonic operation system according to claim 6, wherein the transmission cable includes one or more drive signal transmission lines for transmitting the drive signals and one or more operating signal transmission lines for transmitting the operating signals, and the output plug is removably connected to a hand switch input plug provided at a distal end of the operating signals transmission lines.

8. The ultrasonic operation system according to claim 7, wherein the hand switch input plug is provided at an end of a cable which branches from the transmission cable.

9. The ultrasonic operation system according to claim 7, wherein the hand switch input plug is provided on the socket of the second connector device.

10. The ultrasonic operation system according to claim 9, wherein the hand switch input plug is provided on a shell of the socket so that it can be freely rotated along the circumferential surface of the socket.

11. The ultrasonic operation system according to claim 4, wherein the operating signal output part is a relay adapter which includes a third plug removably attached to the socket of the second connector device and a second socket removably attached to at least one of the second plugs of the second connector device and which is removably interposed between the transmission cable and at least one of the handpieces.

12. The ultrasonic operation system according to claim 1, wherein an identification element is incorporated inside each of the handpieces to distinguish the handpiece itself, and the drive signal generator unit includes a distinguishing device for distinguishing the connected handpiece based on an identification signal output from the identification element.

13. The ultrasonic operation system according to claim 12, wherein the transmission cable includes one or more identification signal transmission lines for transmitting the identification signals, and the distinguishing device receives the identification signals via the identification signal transmission lines.

14. The ultrasonic operation system according to claim 12, wherein the drive signal generator unit includes a control circuit for controlling the drive signal generator circuit based on a result of distinguishing by the distinguishing device.

15. The ultrasonic operation system according to claim 14, wherein the drive signal generator unit includes a display device connected to the control circuit, and the control circuit is responsive to an output of the distinguishing device to display information indicative of the result of distinguishing by the distinguishing device on the display device.

16. An ultrasonic operation system comprising:
   an ultrasonic transducer for generating ultrasonic vibrations;
   a case for housing the ultrasonic transducer;
   a probe coupled to the ultrasonic transducer and extended from a distal end of the case;
   a drive signal generator unit including a drive signal generator circuit for generating drive signals for driving the ultrasonic transducer;
   a transmission cable having a plurality of transmission lines for transmitting the drive signals, the transmission cable being removably connected to the drive signal generator unit;
   a plug including a plurality of electrodes exposed from a rear end of the case for supplying the drive signals transmitted via the transmission cable to the ultrasonic transducer; and
   a socket which has a recess to receive the rear end of the case, the socket being removably connected with the plug for electrically connecting distal ends of the transmission lines to the electrodes respectively.

17. The ultrasonic operation system according to claim 16, wherein the plurality of electrodes are provided in a concentric circular form for allowing relative rotation of the socket and the plug.

18. The ultrasonic operation system according to claim 17, further comprising a locking device comprising a latching projection provided in the plug and a pawl provided in the socket which engages the latching projection, wherein the locking device restricts the movement of the plug and the socket in an attaching and removing direction and retains the plug in the socket.

19. The ultrasonic operation system according to claim 18, wherein the pawl is movable between a position to engage the latching projection and a position not to engage the latching projection.

* * * * *